(12) United States Patent
Busfield et al.

(10) Patent No.: US 7,294,482 B2
(45) Date of Patent: Nov. 13, 2007

(54) EGF-LIKE NUCLEIC ACIDS

(75) Inventors: Samantha J. Busfield, Maddington (AU); David P. Gearing, Doncaster (AU)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 538 days.

(21) Appl. No.: 10/345,764

(22) Filed: Jan. 16, 2003

(65) Prior Publication Data

US 2003/0138912 A1 Jul. 24, 2003

Related U.S. Application Data

(60) Division of application No. 09/443,959, filed on Nov. 19, 1999, now abandoned, which is a continuation-in-part of application No. 09/196,269, filed on Nov. 19, 1998, now abandoned.

(51) Int. Cl.
*C12N 15/12* (2006.01)
*C12N 5/10* (2006.01)
*C12P 21/02* (2006.01)
*C07K 14/47* (2006.01)

(52) U.S. Cl. .......... 435/69.1; 435/71.1; 435/320.1; 435/471; 435/325; 435/255.1; 536/23.5; 530/350

(58) Field of Classification Search ............... 435/69.1, 435/71.1, 320.1, 471, 325; 536/23.5, 24.3; 530/351

See application file for complete search history.

(56) References Cited

U.S. PATENT DOCUMENTS

| | | | |
|---|---|---|---|
| 5,633,147 | A | 5/1997 | Meissner et al. |
| 5,892,012 | A | 4/1999 | Hillman et al. |
| 5,916,769 | A | 6/1999 | Olsen et al. |
| 6,074,841 | A | 6/2000 | Gearing et al. |
| 6,133,423 | A | 10/2000 | Gearing et al. |
| 6,150,502 | A | 11/2000 | Strachan |
| 6,573,095 | B1 * | 6/2003 | Strachan ........... 435/325 |

FOREIGN PATENT DOCUMENTS

| | | |
|---|---|---|
| WO | WO98/07736 | 2/1998 |
| WO | WO99/55865 | 11/1999 |

OTHER PUBLICATIONS

Leigh et al. *Epidermolysus bullosa*: Preliminary Observations of Blister Formation in Keratinocyte Cultures, British Journal of Dermatology, vol. 111, pp. 527-532. 1984.*
Barrandon, Y. and Green, H., "Cell Migration is Essential for Sustained Growth of Keratinocyte Colonies: The Roles of Transforming Growth Factor-α and Epidermal Growth Factor," *Cell*, 50:1131-1137 (1987).
Brown, G.L. et al., "Enhancement of Wound Healing by Topical Treatment with Epidermal Growth Factor," *New Engl. J. Med.*, 321(2):76-79 (1989).
Buckley-Sturrock, A. et al., "Differential Stimulation of Collagenase and Chemotactic Activity in Fibroblasts Derived from Rat Wound Repair Tissue and Human Skin by Growth Factors," *J. Cell. Physiol.*, 138:70-78 (1989).
Burgess, A.W., "Epidermal Growth Factor and Transforming Growth Factor α," *British Medical Bulletin*, 45(2):401-424 (1989).
Carpenter, G. and Wahl, M.I., "The Epidermal Growth Factor Family," In: *Handbook of Experimental Pharmacology, Peptide Growth Factors and Their Receptors 1*, Sporn, M.B. and Roberts, A.B., Eds., (Springer Verlag: New York), vol. 95, Part I, Chapter 4, pp. 69-171 (1990).
Chernoff, E.A.G. and Robertson, S., "Epidermal Growth Factor and the Onset of Epithelial Epidermal Wound Healing," *Tissue & Cell*, 22(2):123-135 (1990).
D'Alfonso, S. and Richiardi, P.M., "A Polymorphic Variation in a Putatiave Regulation Box of the TNFA Promoter Region," *Immunogenetics*, 39:150-154 (1994).
Groenen, L. C. et al., "Structure-Function Relationships for the EGF/TGF-α Family of Mitogens," *Growth Factors*, 11:235-257 (1994).
Kuhnert, P. et al., "The Porcine Tumor Necrosis Factor-Encoding Genes: Sequence and Comparative Analysis," *Gene*, 102:171-178 (1991).
Kwon, J. et al., "Cloning and Sequence Analysis of the Rat Tumor Necrosis Factor-Encoding Genes," *Gene*, 132:227-236 (1993).
Laato, M., "The Effect of the Epidermal Growth Factor on Granulation Tissue Formation in the Rat," *Acta Chirurgica Scandinavica*, 546:7-44 (1998).
Massagué, "Epidermal Growth Factor-Like Transforming Growth Factor," *J. Biol. Chem.*, 258(22):13614-13620 (1983).
Massagué, J. and Pandiella, A., "Membrane-Anchored Growth Factors," *Annu. Rev. Biochem.*, 62:515-541 (1993).

(Continued)

*Primary Examiner*—Elleen O'Hara
*Assistant Examiner*—Fozia Hamud
(74) *Attorney, Agent, or Firm*—Hamilton, Brook, Smith & Reynolds, P.C.

(57) ABSTRACT

The invention provides isolated nucleic acid molecules, designated ELVIS-1, ELVIS-2, and ELVIS-3 (for Epidermal Growth Factor-Like Variant In Skin-1, 2, and 3). ELVIS nucleic acid molecules encode wholly secreted and transmembrane proteins with homology to EGF and TGF-α. The invention also provides antisense nucleic acid molecules, expression vectors containing the nucleic acid molecules of the invention, host cells into which the expression vectors have been introduced, and nonhuman transgenic animals in which a nucleic acid molecule of the invention has been introduced or disrupted. The ELVIS nucleic acids of the present invention are useful as modulating agents in regulating a variety of cellular processes, and are particularly useful for diagnostic, screening and therapeutic methods for the treatment of skin conditions, such as for wound healing. Accordingly, in one aspect, this invention provides isolated nucleic acid molecules encoding a polypeptide of the invention or biologically active portion thereof. The present invention also provides nucleic acid molecules which are suitable as primers or hybridization probes for the detection of nucleic acids encoding a polypeptide of the invention.

35 Claims, 11 Drawing Sheets

OTHER PUBLICATIONS

Nash. A.D. et al., "Molecular Cloning, Expression and Characterization of Ovine TNFα," *Immunology and Cell Biology*, 69:273-283. (1991).

Nedwin, G.E. et al., "Human Lymphotoxin and Tumor Necrosis Factor Genes: Structure, Homology and Chromosomal Localization," *Nucl. Acids Res.*, 13(17):6361-6373 (1985).

Okamura, K. et al., "A Model System for Tumor Angiogenesis: Involvement of Transforming Growth Factor-α in Tube Formation of Human Microvascular Endothelial Cells Induced by Esophageal Cancer Cells," *Biochem. Biophys. Res. Commun.*, 186(3):1471-1479 (1992).

Soler, C. and Carpenter, G., "The Epidermal Growth Factor (EGF) Family," In: *Guidebook to Cytokines and Their Receptors*, Nicola, N.A., Ed., (Oxford University Press: New York, NY), pp. 194-197 (1994).

Ozanne, B. et al, "Over-Expression of the EGF Receptor is a Hallmark of Squamous Cell Carcinomas," *J. Pathol.*, 149:9-14 (1986).

Paulsson, Y. et al., "Possible Positive Autocrine Feedback in the Prereplicative Phase of Human Fibroblasts," *Nature*, 328:715-717 (1987).

Pennica, D. et al., "Human Tumour Necrosis Factor: Precursor Structure, Expression and Homology to Lymphotoxin," *Nature*, 312:724-729 (1984).

Shing, Y. et al., "Betacellulin: A Mitogen From Pancreatic β Cell Tumors," *Science*, 259:1604-1607 (1993).

Semon, D. et al., "Nucleotide Sequence of the Murine TNF Locus, Including the TNF-α (tumor necrosis factor) and TNF-β (lymphotoxin) Genes," *Nucleic Acids Res.*, 15(21):9083-9084 (1987).

Wilson, A.G. et al., "Single Base Polymorphism in the Human Tumor Necrosis Factor Alpha (TNFα) Gene Detectable by NcoI Restriction of PCR Product," *Human Molecular Genetics*, 1(5):353 (1992).

Hillier, L. et al., *EST Database*, Accession No. N39322 (1996).

Fitzgerald, D.J. and Pastan, I., "Recombinant Toxins Directed to Cytokine and Growth Factor Receptors," In: *Clinical Applications of Cytokines—Role in Pathogenesis, Diagnosis, and Therapy*, Oppenheim, J.J. et al., Eds. (Oxford University Press: New York, NY), Chapter 35, pp. 263-265 (1993).

Jyung, R.W. and Mustoe, T.A., "Role of Cytokines in Wound Repair," In: *Clinical Applications of Cytokines—Role in Pathogenesis, Diagnosis, and Therapy*, Oppenheim, J.J. et al., Eds. (Oxford University Press: New York, NY), Chapter 41, pp. 307-327 (1993).

Riese, D.J. and Stern, D.F., "Specificity Within the EGF Family/ ErbB Receptor Family Signaling Network," *BioEssays*, 20:41-48 (1998).

Chapman, S.J. and Eady, R.A., "Blistering in Keratinocyte Cultures: a Regular Phenomenon Associated with Differentiation," *Eur. J. Cell Biol.*, 39(2):352-359 (1986).

* cited by examiner

Nucleotide and Amino Acid Sequences of ELVIS-1

```
  1 GTCGACCCACGCGTCCGAGAAAGTTAAGCAACTACAGGAAATGGCTTTGGGAGTTCCAAT
  1                                            M  A  L  G  V  P  I

61 ATCAGTCTATCTTTTATTCAACGCAATGACAGCACTGACCGAAGAGGCAGCCGTGACTGT
  8  S  V  Y  L  L  F  N  A  M  T  A  L  T  E  E  A  A  V  T  V

121 AACACCTCCAATCACAGCCCAGCAAGGTAACTGGACAGTTAACAAAACAGAAGCTGACAA
 28  T  P  P  I  T  A  Q  Q  G  N  W  T  V  N  K  T  E  A  D  N

181 CATAGAAGGACCCATAGCCTTGAAGTTCTCACACCTTTGCCTGGAAGATCATAACAGTTA
 48  I  E  G  P  I  A  L  K  F  S  H  L  C  L  E  D  H  N  S  Y

241 CTGCATCAACGGTGCTTGTGCATTCCACCATGAGCTAGAGAAAGCCATCTGCAGGTGTTT
 68  C  I  N  G  A  C  A  F  H  H  E  L  E  K  A  I  C  R  C  F

301 TACTGGTTATACTGGAGAAAGGTGTGAGCACTTGACTTTAACTTCATATGCTGTGGATTC
 88  T  G  Y  T  G  E  R  C  E  H  L  T  L  T  S  Y  A  V  D  S

361 TTATGAAAAATACATTGCAATTGGGATTGGTGTTGGATTACTATTAAGTGGTTTTCTTGT
108  Y  E  K  Y  I  A  I  G  I  G  V  G  L  L  L  S  G  F  L  V

421 TATTTTTTACTGCTATATAAGAAAGAGGTGTCTAAAATTGAAATCGCCTTACAATGTCTG
128  I  F  Y  C  Y  I  R  K  R  C  L  K  L  K  S  P  Y  N  V  C

481 TTCTGGAGAAAGACGACCACTGTGAGGCCTTTGTGAAGAATTTTCATCAAGGCATCTGTA
148  S  G  E  R  R  P  L  *

541 GAGATCAGTGAGCCCAAAATTAAAGTTTTCAGATGAAACAACAAAACTTGTCAAGCTGAC

601 TAGACTCGAAAATAATGAAAGTTGGGATCACAATGAAATGAGAAGATAAAATTCAGCGTT

661 GGCCTTTAGACTTTGCCATCCTTAAGGAGTGATGGAAGCCAAGTGAACAAGCCTCAGTGA

721 CACAAGTCAAATTCATAGTTTCACTCTGGGTTTTTTGTTGTTGTGTGGTTATTATTCTCA

781 CTACAGAAAGACTGAGTTTCATGCTCCTGGCTATGTCAGATGTGAATTTTCATGGGAATA

841 ATAATCAACCTTGCAGCAAGCCAAAGCAATGCCTCGCTTGGGTTCTTCATGTTCTTACTA

901 CCCAGCGTTTTTTACCACCTAGATGGGCCTCTCTAAGTCTATTTGCTCAATGAACCTTAT

961 CCCAAACTTGTTGTTTTCATGGTGTCTGAAAGAATGTGATGTCAGCTTTTAGAATGAAAT

1021 CAGTGTTAAGGTACCTCCAGTGAACCAAACATGTGTCTTAAATCTAAGCCACTGAAAACA

1081 GAAGGGAATGTCCAAGGCAAATACAAATCATACACAGCTTGTAACAACATACAGCCTTTC

1141 TATGTGAAATAATGGAATAAACTAAAGAGTTTCTGAAGACTGAAGCTATCTGGATATCAA

1201 GTCTGGAGTAGGCAAAGCATTTCCATTTCTACATGGATTATAAAACTTTGTGTTGGACTC

1261 ATTGGTCCCTAATGCTTTTGTTCATCACTTCTTCCAGTTATCAGTGGAATTACCTGGTGA
```

FIGURE 1

```
1321 CCATTCATTTGGACCGAAATCCTGGAAGTCTCCTACTGAATAAAAGTCTACAATTGGCCC
1381 TAAAATAGAAACTGAAAAACAGGACATAGAATTTTTTCACCAGACCACAGCATGTGGAAA
1441 CTTTCTTTATCATTTTTGAACACTTGTTAACAGATTTGCACATAGAGGGAGAGAAAAAAA
1501 ATGGAGTAACAGTCAAAATAATAATAATCAGTATCCAGGCCAGGCGTGGTGGTTCACGCC
1561 TGTAATCCTAGCACTTTGGGAGGCCGAGGCGGATGGAGCACCTGAGGTCAGGAGTTTGAG
1621 ACCAGCCTGGCCAACATGGTGAAACCCTGTCTCTACTAAAAATACAAAAATTAGCTGGGC
1681 GTGGTGGTGCATGCCTGTAATCCCAGCTACTCCAGAGGCTGACACAGGACAATCACTTGA
1741 ACCCAGGAGGCAGAGGTTGTAGTGAGCCGAGATGGCAACCCTGCACTCCAACCTGGGTGA
1801 CAAGAGCGAAACTCCATCTCAAAAAAAAAAAAAAAAAAAAAAAAAAAAAAGGGCGGCCGC
```

FIGURE 1A

Hydropathy Plot of Human ELVIS-1

>ELVIS-1 S
MALGVPISVYLLFNAMTALTEEAAVTVTPPITAQQGNWTVNKTEADNIEGPIALKFSHLC
LEDHNSYCINGACAFHHELEKAICRCFTGYTGERCEHLTLTSYAVDSYEKYIAIGIGVGL
LLSGFLVIFYCYIRKRCLKLKSPYNVCSGERRPL                       TM

Nucleotide and Amino Acid Sequences of ELVIS-2

```
  1  AGCAACTACAGGAAATGGCTTTGGGAGTTCCAATATCAGTCTATCTTTTATTCAACGCAA
  1                M  A  L  G  V  P  I  S  V  Y  L  L  F  N  A  M

61  TGACAGCACTGACCGAAGAGGCAGCCGTGACTGTAACACCTCCAATCACAGCCCAGCAAG
 17    T  A  L  T  E  E  A  A  V  T  V  T  P  P  I  T  A  Q  Q  A

121  CTGACAACATAGAAGGACCCATAGCCTTGAAGTTCTCACACCTTTGCCTGGAAGATCATA
 37    D  N  I  E  G  P  I  A  L  K  F  S  H  L  C  L  E  D  H  N

181  ACAGTTACTGCATCAACGGTGCTTGTGCATTCCACCATGAGCTAGAGAAAGCCATCTGCA
 57    S  Y  C  I  N  G  A  C  A  F  H  H  E  L  E  K  A  I  C  R

241  GGTGTTTTACTGGTTATACTGGAGAAAGGTGTCTAAAATTGAAATCGCCTTACAATGTCT
 77    C  F  T  G  Y  T  G  E  R  C  L  K  L  K  S  P  Y  N  V  C

301  GTTCTGGAGAAAGACGACCACTGTGAGGCCTTTGTGAAGAATTTTCATCAAGGCATCTGT
 97    S  G  E  R  R  P  L  *

361  AGAGATCAGTGAGCCCAAAATTAAAGTTTTCAGATGAAACAACAAAACTTGTCAAGCTGA

421  CTAGACTCGAAAATAATGAAAGTTGGGATCACAATGAAATGAGAAGA
```

FIGURE 3

Hydropathy Plot for Human ELVIS-2

>37e06pep   S
MALGVPISVYLLFNAMTALTEEAAVTVTPPITAQQADNIEGPIALKFSHLCLEDHNSYCI
NGACAFHHELEKAICRCFTGYTGERCLKLKSPYNVCSGERRP

Nucleotide and Amino Acid Sequences of ELVIS-3

```
1    AACTACAGGAAATGGCTTTGGGAGTTCCAATATCAGTCTATCTTTTATTCAACGCAATGA
1                M   A   L   G   V   P   I   S   V   Y   L   L   F   N   A   M   T

61   CAGCACTGACCGAAGAGGCAGCCGTGACTGTAACACCTCCAATCACAGCCCAGCAAGCTG
18     A   L   T   E   E   A   A   V   T   V   T   P   P   I   T   A   Q   Q   A   D

121  ACAACATAGAAGGACCCATAGCCTTGAAGTTCTCACACCTTTGCCTGGAAGATCATAACA
38     N   I   E   G   P   I   A   L   K   F   S   H   L   C   L   E   D   H   N   S

181  GTTACTGCATCAACGGTGCTTGTGCATTCCACCATGAGCTAGAGAAAGCCATCTGCAGGT
58     Y   C   I   N   G   A   C   A   F   H   H   E   L   E   K   A   I   C   R   C

241  GTCTAAAATTGAAATCGCCTTACAATGTCTGTTCTGGAGAAAGACGACCACTGTGAGGCC
78     L   K   L   K   S   P   Y   N   V   C   S   G   E   R   R   P   L   *

301  TTTGTGAAGAATTTTCATCAAGGCATCTTGTAGAGATCAAGTGAGCCCAAAATTAAAGTT

361  TTCAGATGAAACAACAAAACTTGTCAAGCTGACTAGACTCGAAAATATG
```

FIGURE 5

Hydropathy Plot for ELVIS-3

>64b08pep    S
MALGVPISVYLLFNAMTALTEEAAVTVTPPITAQQADNIEGPIALKFSHLCLEDHNSYCI
NGACAFHHELEKAICRCLKLKSPYNVCSGERRP

Alignment of the Amino Acid Sequences of ELVIS-1, ELVIS-2, ELVIS-3 and Human TGF-α

```
              1                                                                          80
ELVIS-3pep    MALGVPIS.VYLLFNAMTALTEEAAVT.VTPPITAQQ.........ADNIEGPIALKFSHLCLEDHNSYCINGACAFHHE
ELVIS-2pep    MALGVPIS.VYLLFNAMTALTEEAAVT.VTPPITAQQ.........ADNIEGPIALKFSHLCLEDHNSYCINGACAFHHE
ELVIS-1_pep   MALGVPIS.VYLLFNAMTALTEEAAVT.VTPPITAQQGNWTVNKTEADNIEGPIALKFSHLCLEDHNSYCINGACAFHHE
P01135-TGFa   ---MVPSAGQLALFALGIVLAACQALENSTSPLSADP..........PVAAAVVSHFN.DCPDSHTQFCFHGTCRFLVQ
              81                                                                         160
ELVIS-3pep    LEKAICR.................................................CLKLKS.PYN...VCSGER...
ELVIS-2pep    LEKAICRCFTGYTGE..........................................RCLKLKS.PYN...VCSGER...
ELVIS-1_pep   LEKAICRCFTGYTGERCEHLTLTSYAVDSYEKYIAIGIGVGLLLSGFLVIFYCYIRKRCLKLKS.PYN...VCSGER...
P01135-TGFa   EDKPACVCHSGYVGARCEHADLLAVVAASQKKQAITALVVVSIVALAVLIITCVLIHCCQVRKHCEWCRALICRHEKPSA
              161            175
ELVIS-3pep    ....RPL........
ELVIS-2pep    ....RPL........
ELVIS-1_pep   ....RPL........
P01135-TGFa   LLRGRTACCHSETVV
```

FIGURE 7

Alignment of the Nucleotide Sequences of ELVIS-1, ELVIS-2 and ELVIS-3

```
ELVIS-2  jthkf037e06   1 ------------------------------AGCAAC-TACAGGAAATGGCTTTGGGAGTTCCAATATCAGTCTATCTTTATTCAACGCAATGAC  80
ELVIS-3  jthkf064b08     ------------------------------AAC--TACAGGAAATGGCTTTGGGAGTTCCAATATCAGTCTATCTTTATTCAACGCAATGAC
         ELVIS-1         GTCGACCCACGCGTCCGAGAAAGTTAAGCAACTACAGGAAATGGCTTTGGGAGTTCCAATATCAGTCTATCTTTATTCAACCCAATGAC     160 jthkf037e06  81 AGCACTGACCGAAGAGGCAGCCGTGACTGTAACACCTCCAATACAGCCCAGCAAG----------------------------------
         jthkf064b08     AGCACTGACCGAAGAGGCAGCCGTGACTGTAACACCTCCAATACAGCCCAGCAAG
         ELVIS-1         AGCACTGACCGAAGAGGCAGCCGTGACTGTAACACCTCCAATACAGCCCAGCCCAGCAAGTAACTGGACAGTTAACAAAACAG        240 jthkf037e06 161 ---CTGACAACATAGAAGGACCCATAGCCTTGAAGTTCTCACACCTTTGCCTGGAAGATCATAACAGTTACTGCATCAAC
         jthkf064b08     ---CTGACAACATAGAAGGACCCATAGCCTTGAAGTTCTCACACCTTTGCCTGGAAGATCATAACAGTTACTGCATCAAC
         ELVIS-1         AAGCTGACAACATAGAAGGACCCATAGCCTTGAAGTTCTCACACCTTTGCCTGGAAGATCATAACAGTTACTGCATCAAC     320 jthkf037e06 241 GGTGCTTGTGCATTCCACCATGAGCTAGAGAAAGCCATCTGCAGGTGTTTTACTGGTTATACTGGAGAAGGTGT-----
         jthkf064b08     GGTGCTTGTGCATTCCACCATGAGCTAGAGAAAGCCATCTGCAGGTG---T-------------------------
         ELVIS-1         GGTGCTTGTGCATTCCACCATGAGCTAGAGAAAGCCATCTGCAGGTGTTTTACTGGTTATACTGGAGAAGGTGAGCA       400 jthkf037e06 321 CTTGACTTTAACTTCATATGCTGTGGATTCTTATGAAAATACATTGCAATTGGATTGGTGTTGGATTACTATTAAGTG
         jthkf064b08
         ELVIS-1                                                                                                       480 jthkf037e06 401 ------------------------------------------------------------CTAAAATTGAAATCGCCTTACAATGTCTGTTCTGGAGAA
         jthkf064b08                                                                 CTAAAATTGAAATCGCCTTACAATGTCTGTTCTGGAGAA
         ELVIS-1         GTTTTCTTGTTATTTTTACTGCTATATAAGAAAGAGTGTCTAAAATTGAAATCGCCTTACAATGTCTGTTCTGGAGAA           560 jthkf037e06 481 AGACGACCACTGTGAGGCCTTTGTGAAGAATTTCATCAAGGCATCT-GTAGAGATCA-GTGAGCCCAAAATTAAAGTTT
         jthkf064b08     AGACGACCACTGTGAGGCCTTTGTGAAGAATTTCATCAAGGCATCTTGTAGAGATCAAGTGAGCCCAAAATTAAAGTTT
         ELVIS-1         AGACGACCACTGTGAGGCCTTTGTGAAGAATTTCATCAAGGCATCT-GTAGAGATCA-GTGAGCCCAAAATTAAAGTTT
```

FIGURE 8A

Alignment of the Nucleotide Sequences of ELVIS-1, ELVIS-2 and ELVIS-3

```
                 561                                                              640
jthkf037e06      TCAGATGAAACAACAAAACTTGTCAAGCTGACTAGACTCGAAAATAATGAAAGTTGGGATCACAATGAAATGAGAAGA--
jthkf064b08      TCAGATGAAACAACAAAACTTGTCAAGCTGACTAGACTCGAAAATAATGAAAGTTGGGATCACAATGAAATGAGAAGA--
ELVIS-1          TCAGATGAAACAACAAAACTTGTCAAGCTGACTAGACTCGAAAATA-TG-------------------------------

641        646
jthkf037e06      ------
jthkf064b08      ------
ELVIS-1          AAATCA
```

FIGURE 8B

```
acggggtccg agaaagttaa gcaactacag gaa atg gct ttg gga gtt cca ata        54
                                     Met Ala Leu Gly Val Pro Ile
                                      1               5 tca gtc tat ctt tta ttc aac gca atg aca gca ctg acc gaa gag gca        102
Ser Val Tyr Leu Leu Phe Asn Ala Met Thr Ala Leu Thr Glu Glu Ala
         10              15              20 gcc gtg act gta aca cct cca atc aca gcc cag caa gct gac aac ata        150
Ala Val Thr Val Thr Pro Pro Ile Thr Ala Gln Gln Ala Asp Asn Ile
     25              30              35 gaa gga ccc ata gcc ttg aag ttc tca cac ctt tgc ctg gaa gat cat        198
Glu Gly Pro Ile Ala Leu Lys Phe Ser His Leu Cys Leu Glu Asp His
 40              45              50              55 aac agt tac tgc atc aac ggt gct tgt gca ttc cac cat gag cta gag        246
Asn Ser Tyr Cys Ile Asn Gly Ala Cys Ala Phe His His Glu Leu Glu
             60              65              70 aaa gcc atc tgc agg tgt cta aaa ttg aaa tcg cct tac aat gtc tgt        294
Lys Ala Ile Cys Arg Cys Leu Lys Leu Lys Ser Pro Tyr Asn Val Cys
                 75              80              85 tct gga gaa aga cga cca ctg tgaggccttt gtgaagaatt ttcatcaagg           345
Ser Gly Glu Arg Arg Pro Leu
             90 catctgtaga gatcaagtga gcccaaaatt aaagttttca gatgaaacaa caaaacttgt      405
caagctgact agactcgaaa atatggaaag ttggggatca caatgaaatg agaagataaa      465
atcagcggtg gcccttagac tttgccatcc ttaaggagtg atggaagcca agtgaacaag      525
cctcagtgac acaagtcaaa ttcataggtt cactctggg                            564
```

FIGURE 9

SEQUENCE LISTING

<160> NUMBER OF SEQ ID NOS: 24

<210> SEQ ID NO 1

-continued

<211> LENGTH: 1858
<212> TYPE: DNA
<213> ORGANISM: Homo sapiens
<220> FEATURE:
<221> NAME/KEY: CDS
<222> LOCATION: (41)...(502)

<400> SEQUENCE: 1

```
gtcgacccac gcgtccgaga aagttaagca actacaggaa atg gct ttg gga gtt          55
                                              Met Ala Leu Gly Val
                                                1               5 cca ata tca gtc tat ctt tta ttc aac gca atg aca gca ctg acc gaa         103
Pro Ile Ser Val Tyr Leu Leu Phe Asn Ala Met Thr Ala Leu Thr Glu
         10                  15                  20 gag gca gcc gtg act gta aca cct cca atc aca gcc cag caa ggt aac         151
Glu Ala Ala Val Thr Val Thr Pro Pro Ile Thr Ala Gln Gln Gly Asn
 25                  30                  35 tgg aca gtt aac aaa aca gaa gct gac aac ata gaa gga ccc ata gcc         199
Trp Thr Val Asn Lys Thr Glu Ala Asp Asn Ile Glu Gly Pro Ile Ala
             40                  45                  50 ttg aag ttc tca cac ctt tgc ctg gaa gat cat aac agt tac tgc atc         247
Leu Lys Phe Ser His Leu Cys Leu Glu Asp His Asn Ser Tyr Cys Ile
 55                  60                  65 aac ggt gct tgt gca ttc cac cat gag cta gag aaa gcc atc tgc agg         295
Asn Gly Ala Cys Ala Phe His His Glu Leu Glu Lys Ala Ile Cys Arg
 70                  75                  80                  85 tgt ttt act ggt tat act gga gaa agg tgt gag cac ttg act tta act         343
Cys Phe Thr Gly Tyr Thr Gly Glu Arg Cys Glu His Leu Thr Leu Thr
             90                  95                 100 tca tat gct gtg gat tct tat gaa aaa tac att gca att ggg att ggt         391
Ser Tyr Ala Val Asp Ser Tyr Glu Lys Tyr Ile Ala Ile Gly Ile Gly
                105                 110                 115 gtt gga tta cta tta agt ggt ttt ctt gtt att ttt tac tgc tat ata         439
Val Gly Leu Leu Leu Ser Gly Phe Leu Val Ile Phe Tyr Cys Tyr Ile
            120                 125                 130 aga aag agg tgt cta aaa ttg aaa tcg cct tac aat gtc tgt tct gga         487
Arg Lys Arg Cys Leu Lys Leu Lys Ser Pro Tyr Asn Val Cys Ser Gly
        135                 140                 145 gaa aga cga cca ctg tgaggccttt gtgaagaatt ttcatcaagg catctgtaga         542
Glu Arg Arg Pro Leu
150 gatcagtgag cccaaaatta aagttttcag atgaaacaac aaaacttgtc aagctgacta        602 gactcgaaaa taatgaaagt tgggatcaca atgaaatgag aagataaaat tcagcgttgg       662 cctttagact ttgccatcct taaggagtga tggaagccaa gtgaacaagc tcagtgaca        722 caagtcaaat tcatagtttc actctgggtt ttttgttgtt gtgtggttat tattctcact      782 acagaaagac tgagtttcat gctcctggct atgtcagatg tgaattttca tgggaataat     842 aatcaacctt gcagcaagcc aaagcaatgc ctcgcttggg ttcttcatgt tcttactacc     902 cagcgttttt taccacctag atgggcctct ctaagtctat ttgctcaatg aaccttatcc     962 caaacttgtt gttttcatgg tgtctgaaag aatgtgatgt cagcttttag aatgaaatca   1022 gtgttaaggt acctccagtg aaccaaacat gtgtcttaaa tctaagccac tgaaaacaga   1082 agggaatgtc caaggcaaat acaaatcata cacagcttgt aacaacatac agcctttcta   1142 tgtgaaataa tggaataaac taagagtttt ctgaagactg aagctatctg gatatcaagt   1202 ctggagtagg caaagcattt ccatttctac atgattata aaactttgtg ttggactcat    1262 tggtccctaa tgcttttgtt catcacttct tccagttatc agtggaatta cctggtgacc   1322
```

```
attcatttgg accgaaatcc tggaagtctc ctactgaata aaagtctaca attggcccta    1382
aaatagaaac tgaaaacag  gacatagaat tttttcacca gaccacagca tgtggaaact    1442
ttctttatca ttttttgaaca cttgttaaca gatttgcaca tagagggaga gaaaaaaaat   1502
ggagtaacag tcaaaataat aataatcagt atccaggcca ggcgtggtgg ttcacgcctg    1562
taatcctagc actttgggag gccgaggcgg atggagcacc tgaggtcagg agtttgagac    1622
cagcctggcc aacatggtga aaccctgtct ctactaaaaa tacaaaaatt agctgggcgt    1682
ggtggtgcat gcctgtaatc ccagctactc cagaggctga cacaggacaa tcacttgaac    1742
ccaggaggca gaggttgtag tgagccgaga tggcaaccct gcactccaac ctgggtgaca    1802
agagcgaaac tccatctcaa aaaaaaaaaa aaaaaaaaa  aaaaagggc  ggccgc        1858
```

```
<210> SEQ ID NO 2
<211> LENGTH: 154
<212> TYPE: PRT
<213> ORGANISM: Homo sapiens

<400> SEQUENCE: 2

Met Ala Leu Gly Val Pro Ile Ser Val Tyr Leu Leu Phe Asn Ala Met
 1               5                  10                  15

Thr Ala Leu Thr Glu Glu Ala Val Thr Val Thr Pro Pro Ile Thr
             20                  25                  30

Ala Gln Gln Gly Asn Trp Thr Val Asn Lys Thr Glu Ala Asp Asn Ile
         35                  40                  45

Glu Gly Pro Ile Ala Leu Lys Phe Ser His Leu Cys Leu Glu Asp His
     50                  55                  60

Asn Ser Tyr Cys Ile Asn Gly Ala Cys Ala Phe His His Glu Leu Glu
 65                  70                  75                  80

Lys Ala Ile Cys Arg Cys Phe Thr Gly Tyr Thr Gly Glu Arg Cys Glu
                 85                  90                  95

His Leu Thr Leu Thr Ser Tyr Ala Val Asp Ser Tyr Glu Lys Tyr Ile
            100                 105                 110

Ala Ile Gly Ile Gly Val Gly Leu Leu Leu Ser Gly Phe Leu Val Ile
        115                 120                 125

Phe Tyr Cys Tyr Ile Arg Lys Arg Cys Leu Lys Leu Lys Ser Pro Tyr
    130                 135                 140

Asn Val Cys Ser Gly Glu Arg Arg Pro Leu
145                 150
```

```
<210> SEQ ID NO 3
<211> LENGTH: 462
<212> TYPE: DNA
<213> ORGANISM: Homo sapiens

<400> SEQUENCE: 3
atggctttgg gagttccaat atcagtctat cttttattca acgcaatgac agcactgacc     60
gaagaggcag ccgtgactgt aacacctcca atcacagccc agcaaggtaa ctggacagtt    120
aacaaaacag aagctgacaa catagaagga cccatagcct tgaagttctc acacctttgc    180
ctggaagatc ataacagtta ctgcatcaac ggtgcttgtg cattccacca tgagctagag    240
aaagccatct gcaggtgttt tactggttat actggagaaa ggtgtgagca cttgacttta    300
acttcatatg ctgtggattc ttatgaaaaa tacattgcaa ttgggattgg tgttggatta    360
ctattaagtg gttttcttgt tattttttac tgctatataa gaaagaggtg tctaaaattg    420
aaatcgcctt acaatgtctg ttctggagaa agacgaccac tg                      462
```

<210> SEQ ID NO 4
<211> LENGTH: 467
<212> TYPE: DNA
<213> ORGANISM: Homo sapiens
<220> FEATURE:
<221> NAME/KEY: CDS
<222> LOCATION: (15)...(323)

<400> SEQUENCE: 4

```
agcaactaca ggaa atg gct ttg gga gtt cca ata tca gtc tat ctt tta              50
              Met Ala Leu Gly Val Pro Ile Ser Val Tyr Leu Leu
                1               5                  10 ttc aac gca atg aca gca ctg acc gaa gag gca gcc gtg act gta aca             98
Phe Asn Ala Met Thr Ala Leu Thr Glu Glu Ala Ala Val Thr Val Thr
         15                  20                  25 cct cca atc aca gcc cag caa gct gac aac ata gaa gga ccc ata gcc            146
Pro Pro Ile Thr Ala Gln Gln Ala Asp Asn Ile Glu Gly Pro Ile Ala
     30                  35                  40 ttg aag ttc tca cac ctt tgc ctg gaa gat cat aac agt tac tgc atc            194
Leu Lys Phe Ser His Leu Cys Leu Glu Asp His Asn Ser Tyr Cys Ile
 45                  50                  55                  60 aac ggt gct tgt gca ttc cac cat gag cta gag aaa gcc atc tgc agg            242
Asn Gly Ala Cys Ala Phe His His Glu Leu Glu Lys Ala Ile Cys Arg
                 65                  70                  75 tgt ttt act ggt tat act gga gaa agg tgt cta aaa ttg aaa tcg cct            290
Cys Phe Thr Gly Tyr Thr Gly Glu Arg Cys Leu Lys Leu Lys Ser Pro
             80                  85                  90 tac aat gtc tgt tct gga gaa aga cga cca ctg tgaggccttt gtgaagaatt          343
Tyr Asn Val Cys Ser Gly Glu Arg Arg Pro Leu
         95                 100 ttcatcaagg catctgtaga gatcagtgag cccaaaatta aagttttcag atgaaacaac          403
aaaacttgtc aagctgacta gactcgaaaa taatgaaagt tgggatcaca atgaaatgag          463
aaga                                                                      467
```

<210> SEQ ID NO 5
<211> LENGTH: 103
<212> TYPE: PRT
<213> ORGANISM: Homo sapiens

<400> SEQUENCE: 5

```
Met Ala Leu Gly Val Pro Ile Ser Val Tyr Leu Leu Phe Asn Ala Met
  1               5                  10                  15

Thr Ala Leu Thr Glu Glu Ala Ala Val Thr Val Thr Pro Pro Ile Thr
             20                  25                  30

Ala Gln Gln Ala Asp Asn Ile Glu Gly Pro Ile Ala Leu Lys Phe Ser
         35                  40                  45

His Leu Cys Leu Glu Asp His Asn Ser Tyr Cys Ile Asn Gly Ala Cys
     50                  55                  60

Ala Phe His His Glu Leu Glu Lys Ala Ile Cys Arg Cys Phe Thr Gly
 65                  70                  75                  80

Tyr Thr Gly Glu Arg Cys Leu Lys Leu Lys Ser Pro Tyr Asn Val Cys
                 85                  90                  95

Ser Gly Glu Arg Arg Pro Leu
            100
```

<210> SEQ ID NO 6
<211> LENGTH: 309
<212> TYPE: DNA

<213> ORGANISM: Homo sapiens

<400> SEQUENCE: 6

```
atggctttgg gagttccaat atcagtctat cttttattca acgcaatgac agcactgacc    60
gaagaggcag ccgtgactgt aacacctcca atcacagccc agcaagctga caacatagaa   120
ggacccatag ccttgaagtt ctcacacctt tgcctggaag atcataacag ttactgcatc   180
aacggtgctt gtgcattcca ccatgagcta gagaaagcca tctgcaggtg ttttactggt   240
tatactggag aaaggtgtct aaaattgaaa tcgccttaca atgtctgttc tggagaaaga   300
cgaccactg                                                            309
```

<210> SEQ ID NO 7
<211> LENGTH: 409
<212> TYPE: DNA
<213> ORGANISM: Homo sapiens
<220> FEATURE:
<221> NAME/KEY: CDS
<222> LOCATION: (12)...(293)

<400> SEQUENCE: 7

```
aactacagga a atg gct ttg gga gtt cca ata tca gtc tat ctt tta ttc     50
            Met Ala Leu Gly Val Pro Ile Ser Val Tyr Leu Leu Phe
              1               5                  10 aac gca atg aca gca ctg acc gaa gag gca gcc gtg act gta aca cct     98
Asn Ala Met Thr Ala Leu Thr Glu Glu Ala Ala Val Thr Val Thr Pro
         15                  20                  25 cca atc aca gcc cag caa gct gac aac ata gaa gga ccc ata gcc ttg    146
Pro Ile Thr Ala Gln Gln Ala Asp Asn Ile Glu Gly Pro Ile Ala Leu
 30                  35                  40                  45 aag ttc tca cac ctt tgc ctg gaa gat cat aac agt tac tgc atc aac    194
Lys Phe Ser His Leu Cys Leu Glu Asp His Asn Ser Tyr Cys Ile Asn
                 50                  55                  60 ggt gct tgt gca ttc cac cat gag cta gag aaa gcc atc tgc agg tgt    242
Gly Ala Cys Ala Phe His His Glu Leu Glu Lys Ala Ile Cys Arg Cys
             65                  70                  75 cta aaa ttg aaa tcg cct tac aat gtc tgt tct gga gaa aga cga cca    290
Leu Lys Leu Lys Ser Pro Tyr Asn Val Cys Ser Gly Glu Arg Arg Pro
         80                  85                  90 ctg tgaggccttt gtgaagaatt ttcatcaagg catcttgtag agatcaagtg         343
Leu agcccaaaat taaagttttc agatgaaaca acaaaacttg tcaagctgac tagactcgaa   403
aatatg                                                              409
```

<210> SEQ ID NO 8
<211> LENGTH: 94
<212> TYPE: PRT
<213> ORGANISM: Homo sapiens

<400> SEQUENCE: 8

```
Met Ala Leu Gly Val Pro Ile Ser Val Tyr Leu Leu Phe Asn Ala Met
  1               5                  10                  15

Thr Ala Leu Thr Glu Glu Ala Ala Val Thr Val Thr Pro Pro Ile Thr
             20                  25                  30

Ala Gln Gln Ala Asp Asn Ile Glu Gly Pro Ile Ala Leu Lys Phe Ser
         35                  40                  45

His Leu Cys Leu Glu Asp His Asn Ser Tyr Cys Ile Asn Gly Ala Cys
     50                  55                  60

Ala Phe His His Glu Leu Glu Lys Ala Ile Cys Arg Cys Leu Lys Leu
```

```
                65                  70                  75                  80
Lys Ser Pro Tyr Asn Val Cys Ser Gly Glu Arg Arg Pro Leu
                    85                  90

<210> SEQ ID NO 9
<211> LENGTH: 282
<212> TYPE: DNA
<213> ORGANISM: Homo sapiens

<400> SEQUENCE: 9
atggctttgg gagttccaat atcagtctat cttttattca acgcaatgac agcactgacc      60
gaagaggcag ccgtgactgt aacacctcca atcacagccc agcaagctga caacatagaa     120
ggacccatag ccttgaagtt ctcacacctt tgcctggaag atcataacag ttactgcatc     180
aacggtgctt gtgcattcca ccatgagcta gagaaagcca tctgcaggtg tctaaaattg     240
aaatcgcctt acaatgtctg ttctggagaa agacgaccac tg                       282

<210> SEQ ID NO 10
<211> LENGTH: 21
<212> TYPE: PRT
<213> ORGANISM: Homo sapiens

<400> SEQUENCE: 10

Arg Lys Arg Cys Leu Lys Leu Lys Ser Pro Tyr Asn Val Cys Ser Gly
1               5                   10                  15

Glu Arg Arg Pro Leu
            20

<210> SEQ ID NO 11
<211> LENGTH: 23
<212> TYPE: PRT
<213> ORGANISM: Homo sapiens

<400> SEQUENCE: 11

Tyr Ile Ala Ile Gly Ile Gly Val Gly Leu Leu Ser Gly Phe Leu
1               5                   10                  15

Val Ile Phe Tyr Cys Tyr Ile
            20

<210> SEQ ID NO 12
<211> LENGTH: 90
<212> TYPE: PRT
<213> ORGANISM: Homo sapiens

<400> SEQUENCE: 12

Glu Glu Ala Ala Val Thr Val Thr Pro Pro Ile Thr Ala Gln Gln Gly
1               5                   10                  15

Asn Trp Thr Val Asn Lys Thr Glu Ala Asp Asn Ile Glu Gly Pro Ile
            20                  25                  30

Ala Leu Lys Phe Ser His Leu Cys Leu Glu Asp His Asn Ser Tyr Cys
        35                  40                  45

Ile Asn Gly Ala Cys Ala Phe His His Glu Leu Glu Lys Ala Ile Cys
    50                  55                  60

Arg Cys Phe Thr Gly Tyr Thr Gly Glu Arg Cys Glu His Leu Thr Leu
65                  70                  75                  80

Thr Ser Tyr Ala Val Asp Ser Tyr Glu Lys
                85                  90

<210> SEQ ID NO 13
```

<211> LENGTH: 160
<212> TYPE: PRT
<213> ORGANISM: Homo sapiens

<400> SEQUENCE: 13

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
            20                  25                  30

Asp Pro Pro Val Ala Ala Val Val Ser His Phe Asn Asp Cys Pro
        35                  40                  45

Asp Ser His Thr Gln Phe Cys Phe His Gly Thr Cys Arg Phe Leu Val
    50                  55                  60

Gln Glu Asp Lys Pro Ala Cys Val Cys His Ser Gly Tyr Val Gly Ala
65                  70                  75                  80

Arg Cys Glu His Ala Asp Leu Leu Ala Val Ala Ala Ser Gln Lys
            85                  90                  95

Lys Gln Ala Ile Thr Ala Leu Val Val Val Ser Ile Val Ala Leu Ala
            100                 105                 110

Val Leu Ile Ile Thr Cys Val Leu Ile His Cys Cys Gln Val Arg Lys
        115                 120                 125

His Cys Glu Trp Cys Arg Ala Leu Ile Cys Arg His Glu Lys Pro Ser
    130                 135                 140

Ala Leu Leu Lys Gly Arg Thr Ala Cys His Ser Glu Thr Val Val
145                 150                 155                 160

<210> SEQ ID NO 14
<211> LENGTH: 20
<212> TYPE: PRT
<213> ORGANISM: Homo sapiens

<400> SEQUENCE: 14

Met Ala Leu Gly Val Pro Ile Ser Val Tyr Leu Leu Phe Asn Ala Met
1               5                   10                  15

Thr Ala Leu Thr
            20

<210> SEQ ID NO 15
<211> LENGTH: 36
<212> TYPE: PRT
<213> ORGANISM: Homo sapiens

<400> SEQUENCE: 15

Cys Leu Glu Asp His Asn Ser Tyr Cys Ile Asn Gly Ala Cys Ala Phe
1               5                   10                  15

His His Glu Leu Glu Lys Ala Ile Cys Arg Cys Phe Thr Gly Tyr Thr
            20                  25                  30

Gly Glu Arg Cys
            35

<210> SEQ ID NO 16
<211> LENGTH: 37
<212> TYPE: PRT
<213> ORGANISM: Homo sapiens

<400> SEQUENCE: 16

Cys Leu Glu Asp His Asn Ser Tyr Cys Ile Asn Gly Ala Cys Ala Phe
1               5                   10                  15

His His Glu Leu Glu Lys Ala Ile Cys Arg Cys Phe Thr Gly Tyr Thr
            20                  25                  30

```
                    20                  25                  30

Gly Glu Arg Cys Leu
            35

<210> SEQ ID NO 17
<211> LENGTH: 36
<212> TYPE: PRT
<213> ORGANISM: Homo sapiens

<400> SEQUENCE: 17

Cys Leu Glu Asp His Asn Ser Tyr Cys Ile Asn Gly Ala Cys Ala Phe
 1               5                  10                  15

His His Glu Leu Glu Lys Ala Ile Cys Arg Cys Leu Lys Leu Lys Ser
                20                  25                  30

Pro Tyr Asn Val
            35

<210> SEQ ID NO 18
<211> LENGTH: 124
<212> TYPE: PRT
<213> ORGANISM: Homo sapiens

<400> SEQUENCE: 18

Glu Glu Ala Ala Val Thr Val Thr Pro Pro Ile Thr Ala Gln Gln Gly
 1               5                  10                  15

Asn Trp Thr Val Asn Lys Thr Glu Ala Asp Asn Ile Glu Gly Pro Ile
                20                  25                  30

Ala Leu Lys Phe Ser His Leu Cys Leu Glu Asp His Asn Ser Tyr Cys
                35                  40                  45

Ile Asn Gly Ala Cys Ala Phe His His Glu Leu Glu Lys Ala Ile Cys
            50                  55                  60

Arg Cys Phe Thr Gly Tyr Thr Gly Glu Arg Cys Glu His Leu Thr Leu
65                  70                  75                  80

Thr Ser Tyr Ala Val Asp Ser Tyr Glu Lys Tyr Ile Ala Ile Gly Ile
                85                  90                  95

Gly Val Gly Leu Leu Leu Ser Gly Phe Leu Val Ile Phe Tyr Cys Tyr
                100                 105                 110

Ile Arg Lys Arg Cys Leu Lys Leu Lys Ser Pro Tyr
                115                 120

<210> SEQ ID NO 19
<211> LENGTH: 82
<212> TYPE: PRT
<213> ORGANISM: Homo sapiens

<400> SEQUENCE: 19

Glu Glu Ala Ala Val Thr Val Thr Pro Pro Ile Thr Ala Gln Gln Ala
 1               5                  10                  15

Asp Asn Ile Glu Gly Pro Ile Ala Leu Lys Phe Ser His Leu Cys Leu
                20                  25                  30

Glu Asp His Asn Ser Tyr Cys Ile Asn Gly Ala Cys Ala Phe His His
                35                  40                  45

Glu Leu Glu Lys Ala Ile Cys Arg Cys Phe Thr Gly Tyr Thr Gly Glu
            50                  55                  60

Arg Cys Leu Lys Leu Ser Pro Tyr Asn Val Cys Ser Gly Glu Arg Arg
65                  70                  75                  80

Pro Leu
```

-continued

```
<210> SEQ ID NO 20
<211> LENGTH: 74
<212> TYPE: PRT
<213> ORGANISM: Homo sapiens

<400> SEQUENCE: 20

Glu Glu Ala Ala Val Thr Val Thr Pro Pro Ile Thr Ala Gln Gln Ala
 1               5                  10                  15

Asp Asn Ile Glu Gly Pro Ile Ala Leu Lys Phe Ser His Leu Cys Leu
            20                  25                  30

Glu Asp His Asn Ser Tyr Cys Ile Asn Gly Ala Cys Ala Phe His His
        35                  40                  45

Glu Leu Glu Lys Ala Ile Cys Arg Cys Leu Lys Leu Lys Ser Pro Tyr
    50                  55                  60

Asn Val Cys Ser Gly Glu Arg Arg Pro Leu
65                  70

<210> SEQ ID NO 21
<211> LENGTH: 564
<212> TYPE: DNA
<213> ORGANISM: Homo sapiens

<400> SEQUENCE: 21 acgggtccg agaaagttaa gcaactacag gaaatggctt tgggagttcc aatatcagtc      60
tatcttttat tcaacgcaat gacagcactg accgaagagg cagccgtgac tgtaacacct    120
ccaatcacag cccagcaagc tgacaacata gaaggaccca tagccttgaa gttctcacac    180
ctttgcctgg aagatcataa cagttactgc atcaacggtg cttgtgcatt ccaccatgag    240
ctagagaaag ccatctgcag gtgtctaaaa ttgaaatcgc cttacaatgt ctgttctgga    300
gaaagacgac cactgtgagg cctttgtgaa gaattttcat caaggcatct gtagagatca    360
agtgagccca aaattaaagt tttcagatga acaacaaaa cttgtcaagc tgactagact    420
cgaaaatatg gaaagttggg gatcacaatg aaatgagaag ataaaatcag cggtggccct    480
tagactttgc catccttaag gagtgatgga agccaagtga acaagcctca gtgacacaag    540
tcaaattcat aggttcactc tggg                                            564

<210> SEQ ID NO 22
<211> LENGTH: 13
<212> TYPE: PRT
<213> ORGANISM: Artificial Sequence
<220> FEATURE:
<223> OTHER INFORMATION: peptide used to generate polyclonal antibody

<400> SEQUENCE: 22

Leu Cys Leu Glu Asp His Asn Ser Tyr Cys Ile Asn Gly
 1               5                  10

<210> SEQ ID NO 23
<211> LENGTH: 13
<212> TYPE: PRT
<213> ORGANISM: Artificial Sequence
<220> FEATURE:
<223> OTHER INFORMATION: peptide used to generate polyclonal antibody

<400> SEQUENCE: 23

Gly Tyr Thr Gly Glu Arg Cys Glu His Leu Thr Leu Thr
 1               5                  10

<210> SEQ ID NO 24
```

```
-continued

<211> LENGTH: 15
<212> TYPE: PRT
<213> ORGANISM: Artificial Sequence
<220> FEATURE:
<223> OTHER INFORMATION: peptide used to generate polyclonal antibody

<400> SEQUENCE: 24

Leu Lys Ser Pro Tyr Asn Val Cys Ser Gly Glu Arg Arg Pro Leu
1               5                   10                  15
```

EGF-LIKE NUCLEIC ACIDS

This is a division, and claims the benefit of priority under 35 U.S.C. §120, of U.S. application Ser. No. 09/443,959, filed Nov. 19, 1999, now abandoned which is a continuation-in-part of application Ser. No. 09/196,269, filed Nov. 19, 1998, now abandoned each of which is incorporated by reference herein in its entirety.

BACKGROUND OF THE INVENTION

Epidermal growth factor (EGF) and transforming growth factor-CL (TGF-α) are ligands which interact with the same cell surface receptor, EGF-receptor, and which act as mitogens for a variety of tissues. Groenen et al. (1994) *Growth Factors* 11:235-257. Based on sequence similarity, mitogenic activity, and the ability to interact with the EGF-receptor, several other EGF family members have been identified including amphiregulin, heparin-binding EGF (HB-EGF), and betacellulin. Carpenter et al. (1990) *Handbook Exptl. Pharmacol.* 95(1):69-171; Massague et al. (1993) *Ann. Rev. Biochem.* 62:515-541; Shing et al. (1993) *Science* 259:1604-1607.

Both EGF and TGF-α have been associated with a variety of processes ranging from wound healing to carcinogenesis. Burgess et al. (1989) *Br. Med. Bull.* 45:401-424; Massague et al. (1983) *J. Biol. Chem.* 258:13614-13620; Ozanne et al. (1986) *J. Pathol.* 149:9-14.

In particular, EGF and TGF-α both induce proliferation of dermal fibroblasts. Buckley-Sturrock et al. (1989) *J. Cell. Physiol.* 138:70-78; Laato et al. (1987) *J. Biochem.* 247: 385-388; Paulsson et al. (1987) *Nature* 328:715-717. In addition, EGF exerts proliferative and chemotactic effects on granulation-tissue-derived fibroblasts and induces collagenase and hyaluronic acid synthesis. Laato (1988) *Acta. Chir. Scand. Suppl.* 546:4-44. EGF has also been reported to stimulate keratinocyte proliferation and migration in vitro, further implicating an important role for EGF in the reepithelialization of wounds. Barrandon et al. (1987) *Cell* 50:1131-1137; Chernoff (1990) *Tissue Cell.* 22:123-135.

A number of different cancer cell lines exhibit elevated levels of EGF receptors and TGF-α has been implicated as an autocrine growth factor for many carcinomas. Groenen et al. (1994) *Growth Factors* 11:235-257. Tumour-derived TGF-α is angiogenic, and it has been predicted that an antagonist of TGF-α may inhibit tumour angiogenesis and/or inhibit the growth of a carcinoma. Groenen et al. (1994) *Growth Factors* 11:235-257; Okamura et al. (1992) *Biochem. Biophys. Res. Comm.* 186:1471-1479.

SUMMARY OF THE INVENTION

The present invention is based, at least in part, on the discovery of cDNA molecules which encode a novel family of proteins having significant identity to transforming growth factor alpha (TGF-α) and epidermal growth factor (EGF), referred to herein as the epidermal growth factor-like variant in skin proteins ("ELVIS" family or "ELVIS" proteins). Described below are cDNA molecules encoding human ELVIS-1 (also referred to herein as "TANGO 225" or "T225") and splice variants thereof, referred to as ELVIS-2 and ELVIS-3 (also referred to herein as "T225v1" and "T225v2", respectively). These proteins, fragments, derivatives, and variants thereof are collectively referred to as "polypeptides of the invention" or "proteins of the invention." Nucleic acid molecules encoding polypeptides of the invention are collectively referred to as "nucleic acids of the invention."

The nucleic acids and polypeptides of the present invention are useful as modulating agents in regulating a variety of cellular processes. Accordingly, in one aspect, this invention provides isolated nucleic acid molecules encoding a polypeptide of the invention or a biologically active portion thereof. The present invention also provides nucleic acid molecules which are suitable as primers or hybridization probes for the detection of nucleic acids encoding a polypeptide of the invention.

The invention features nucleic acid molecules which are at least 45% (or 55%, 65%, 75%, 85%, 95%, or 98%) identical to the nucleotide sequence of SEQ ID NO: 1, 3, 4, 6, 7, 9, or the nucleotide sequence of the cDNA insert of a clone deposited with the ATCC as any of Accession Numbers 98981, 98982, and 98983 (the "cDNA of any of ATCC 98981, 98982, and 98983"), or complement thereof.

The invention features nucleic acid molecules which include a fragment of at least 300 (325, 350, 375, 400, 425, 450, 500, 550, 600, 650, 700, 800, 900, 1000, or 1200) nucleotides of the nucleotide sequence of SEQ ID NO:1, 3, 4, 6, 7, 9 or the nucleotide sequence of the cDNA of any of ATCC Accession Numbers 98981, 98982, and 98983, or complement thereof.

The invention also features nucleic acid molecules which include a nucleotide sequence encoding a protein having an amino acid sequence that is at least 45% (or 55%, 65%, 75%, 85%, 95%, or 98%) identical to the amino acid sequence of SEQ ID NO:2, 5, 8, or the amino acid sequence encoded by the cDNA of any of ATCC Accession Numbers 98981, 98982, and 98983, or a complement thereof.

In preferred embodiments, the nucleic acid molecules have the nucleotide sequence of SEQ ID NO:1, 3, 4, 6, 7, 9, or the nucleotide sequence of the cDNA ofany of ATCC Accession Numbers 98981, 98982, and 98983.

Also within the invention are nucleic acid molecules which encode a fragment of a polypeptide having the amino acid sequence of SEQ ID NO:2, 5, or 8, or a fragment including at least 15 (25, 30, 50, 100, 150, 300, or 400) contiguous amino acids of SEQ ID NO:2, 5, 8, or the amino acid encoded by the cDNA of any of ATCC Accession Numbers 98981, 98982, and 98983.

The invention includes nucleic acid molecules which encode a naturally occurring allelic variant of a polypeptide comprising the amino acid sequence of SEQ ID NO:2, 5, 8, or the amino acid sequence encoded by the cDNA of any of ATCC Accession Numbers 98981, 98982, and 98983, wherein the nucleic acid molecule hybridizes to a nucleic acid molecule comprising the nucleic acid sequence encoding the amino acid sequence of SEQ ID NO:2, 5, 8, or the amino acid sequence encoded by the cDNA of any of ATCC Accession Numbers 98981, 98982, and 98983, or complement thereof under stringent conditions.

Also within the invention are isolated polypeptides or proteins having an amino acid sequence that is at least about 60%, preferably 65%, 75%, 85%, 95%, or 98% identical to the amino acid sequence of SEQ ID NO:2, 5, 8, or the amino acid encoded by the cDNA of any of ATCC Accession Numbers 98981, 98982, and 98983.

Also within the invention are isolated polypeptides or proteins which are encoded by a nucleic acid molecule having a nucleotide sequence that is at least about 60%, preferably 65%, 75%, 85%, or 95% identical the nucleic acid sequence encoding SEQ ID NO:2, 5, or 8 and isolated polypeptides or proteins which are encoded by a nucleic acid molecule having a nucleotide sequence which hybridizes under stringent hybridization conditions to a nucleic acid molecule having the nucleotide sequence of SEQ ID NO:1, 3, 4, 6, 7, 9, or complement thereof or the non-coding strand of the cDNA of any of ATCC Accession Numbers 98981, 98982, and 98983.

Also within the invention are polypeptides which are naturally occurring allelic variants of a polypeptide that includes the amino acid sequence of SEQ ID NO:2, 5, 8, or the amino acid sequence encoded by the cDNA of any of ATCC Accession Numbers 98981, 98982, and 98983, wherein the polypeptide is encoded by a nucleic acid molecule which hybridizes to a nucleic acid molecule comprising SEQ ID NO:1, 3, 4, 6, 7, 9, or complement thereof under stringent conditions.

The invention also features nucleic acid molecules that hybridize under stringent conditions to a nucleic acid molecule comprising the nucleotide sequence of SEQ ID NO:1, 3, 4, 6, 7, 9, the cDNA of any of ATCC Accession Numbers 98981, 98982, and 98983, or complement thereof. In other embodiments, the nucleic acid molecules are at least 300 (325, 350, 375, 400, 425, 450, 500, 550, 600, 650, 700, 800, 900, 1000, or 1290) nucleotides in length and hybridize under stringent conditions to a nucleic acid molecule comprising the nucleotide sequence of SEQ ID NO:1, 3, 4, 6, 7, 9, the cDNA of any of ATCC Accession Numbers 98981, 98982, and 98983, or complement thereof.

In one embodiment, the isolated nucleic acid molecules encode an extracellular domain (SEQ ID NO:12), a transmembrane domain (SEQ ID NO:11), and/or a cytoplasmic domain (SEQ ID NO:10) of a polypeptide of the invention. In another embodiment, the invention provides an isolated nucleic acid molecule which is antisense to the coding strand of a nucleic acid of the invention.

Another aspect of the invention provides vectors, e.g., recombinant expression vectors, comprising a nucleic acid molecule of the invention. In another embodiment the invention provides host cells containing such a vector or a nucleic acid molecule of the invention. The invention also provides methods for producing a polypeptide of the invention by culturing, in a suitable medium, a host cell of the invention containing a recombinant expression vector such that a polypeptide is produced.

Another aspect of this invention features isolated or recombinant proteins and polypeptides of the invention. Preferred proteins and polypeptides possess at least one biological activity possessed by the corresponding naturally-occurring human polypeptide. An activity, a biological activity, and a functional activity of a polypeptide or nucleic acid of the invention refers to an activity exerted by, a protein, polypeptide or nucleic acid molecule of the invention on a responsive cell as determined in vivo, or in vitro, according to standard techniques. Such activities can be a direct activity, such as an association with or an enzymatic activity on a second protein or an indirect activity, such as a cellular signaling activity mediated by interaction of the protein with a second protein. Thus, such activities include, e.g., (1) the ability to form protein-protein interactions with proteins in the signaling pathway of the naturally-occurring polypeptide; (2) the ability to bind a ligand of the naturally-occurring polypeptide; (3) the interaction of an ELVIS protein with a receptor. Other activities include: (1) the ability to modulate cellular proliferation; (2) the ability to modulate cellular migration and chemotaxis; (3) the ability to modulate cellular differentiation; (4) the ability to modulate angiogenesis; (5) the ability to modulate epithelial cell proliferation and/or differentiation; and (6) the ability to modulate keritinocyte proliferation and/or differentiation.

In one embodiment, a polypeptide of the invention has an amino acid sequence sufficiently identical to an identified domain of a polypeptide of the invention. As used herein, the term "sufficiently identical" refers to a first amino acid or nucleotide sequence which contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 60% identity, preferably 65% identity, more preferably 75%, 85%, 95%, 98% or more identity are defined herein as sufficiently identical. In one embodiment, an ELVIS protein includes an EGF domain. In another embodiment, an ELVIS protein includes a signal sequence. In yet another embodiment, an ELVIS protein includes an EGF domain, a signal sequence and is secreted. In another embodiment, an ELVIS protein includes a transmembrane domain. In yet another embodiment, an ELVIS protein includes an EGF domain, a transmembrane domain, a signal sequence, and is a membrane bound protein.

In one embodiment, the isolated polypeptides lack both a transmembrane and a cytoplasmic domain. In another embodiment, the polypeptide lacks both a transmembrane domain and a cytoplasmic domain and is soluble under physiological conditions.

In another embodiment, a nucleic acid molecule of the present invention encodes an ELVIS protein which includes a epidermal growth factor (EGF) domain. In another embodiment, a nucleic acid molecule of the present invention encodes an ELVIS protein which includes a signal sequence. In another embodiment, a nucleic acid molecule of the present invention encodes an ELVIS protein which includes an EGF domain and a signal sequence. In yet another embodiment, a nucleic acid molecule of the present invention encodes an ELVIS protein which includes a transmembrane domain.

The polypeptides of the present invention, or biologically active portions thereof, can be operably linked to a heterologous amino acid sequence to form fusion proteins. The invention further features antibodies that specifically bind a polypeptide of the invention such as monoclonal or polyclonal antibodies. In addition, the polypeptides of the invention or biologically active portions thereof can be incorporated into pharmaceutical compositions, which optionally include pharmaceutically acceptable carriers.

In another aspect, the present invention provides methods for detecting the presence of the activity or expression of a polypeptide of the invention in a biological sample by contacting the biological sample with an agent capable of detecting an indicator of activity such that the presence of activity is detected in the biological sample.

In another aspect, the invention provides methods for modulating activity of a polypeptide of the invention comprising contacting a cell with an agent that modulates (inhibits or stimulates) the activity or expression of a polypeptide of the invention such that activity or expression in the cell is modulated. In one embodiment, the agent is an antibody that specifically binds to a polypeptide of the invention.

In another embodiment, the agent modulates expression of a polypeptide of the invention by modulating transcription, splicing, or translation of an mRNA encoding a polypeptide of the invention. In yet another embodiment, the agent is a nucleic acid molecule having a nucleotide sequence that is antisense to the coding strand of an mRNA encoding a polypeptide of the invention.

The present invention also provides methods to treat a subject having a disorder characterized by aberrant activity of a polypeptide of the invention or aberrant expression of a nucleic acid of the invention by administering an agent which is a modulator of the activity of a polypeptide of the invention or a modulator of the expression of a nucleic acid of the invention to the subject. In one embodiment, the modulator is a protein of the invention. In another embodiment, the modulator is a nucleic acid of the invention. In other embodiments, the modulator is a peptide, peptidomimetic, or other small molecule.

The present invention also provides diagnostic assays for identifying the presence or absence of a genetic lesion or mutation characterized by at least one of: (i) aberrant modification or mutation of a gene encoding a polypeptide of the invention, (ii) misregulation of a gene encoding a polypeptide of the invention, and (iii) aberrant post-translational modification of the invention wherein a wild-type form of the gene encodes a protein having the activity of the polypeptide of the invention.

In another aspect, the invention provides a method for identifying a compound that binds to or modulates the activity of a polypeptide of the invention. In general, such methods entail measuring a biological activity of the polypeptide in the presence and absence of a test compound and identifying those compounds which alter the activity of the polypeptide.

The invention also features methods for identifying a compound which modulates the expression of a polypeptide or nucleic acid of the invention by measuring the expression of the polypeptide or nucleic acid in the presence and absence of the compound.

Other features and advantages of the invention will be apparent from the following detailed description and claims.

BRIEF DESCRIPTION OF THE DRAWINGS

FIG. 1 depicts the cDNA sequence of human ELVIS-1 (SEQ ID NO:1) and the predicted amino acid sequence of ELVIS-1 (SEQ ID NO:2). The open reading frame of SEQ ID NO:1 extends from nucleotide 41 to nucleotide 502 of SEQ ID NO:1 (SEQ ID NO:3).

FIG. 3 depicts the cDNA sequence of ELVIS-2 (SEQ ID NO:4), a variant of ELVIS-1, and the predicted amino acid sequence of ELVIS-2 (SEQ ID NO:5), a variant of ELVIS-1. The open reading frame of SEQ ID NO:4 extends from nucleotide 15 to nucleotide 323 of SEQ ID NO:4 (SEQ ID NO:6).

FIG. 5 depicts the cDNA sequence of ELVIS-3 (SEQ ID NO:7), another variant of ELVIS-1, and the predicted amino acid sequence of ELVIS-3 (SEQ ID NO:8). The open reading frame of SEQ ID NO:7 extends from nucleotide 12 to nucleotide 294 of SEQ ID NO:7 (SEQ ID NO:9).

FIG. 7 depicts an alignment of the amino acid sequences of human ELVIS-1 (SEQ ID NO:2), human ELVIS-2 (SEQ ID NO:5), human ELVIS-3 (SEQ ID NO:8) and the amino acid sequence of human TGF-α (SEQ ID NO:13). The amino acid sequences of human ELVIS-1 and human TGF-α have 24.4% sequence identity. The multiple alignment was performed using the ClustalW alignment program with a PAM250 scoring matrix, a Gap Penalty of 10 and a Gap Extension Penalty of 0.05.

FIGS. 8A and 8B depict an alignment of the nucleotide sequences encoding human ELVIS-1 (SEQ ID NO:1), encoding ELVIS-2 (SEQ ID NO:4) and encoding ELVIS-3 (SEQ ID NO:7).

FIG. 9 depicts a more complete sequence (SEQ ID NO:21) of the ELVIS-3 cDNA depicted in FIG. 5.

DETAILED DESCRIPTION OF THE INVENTION

Figure 2:
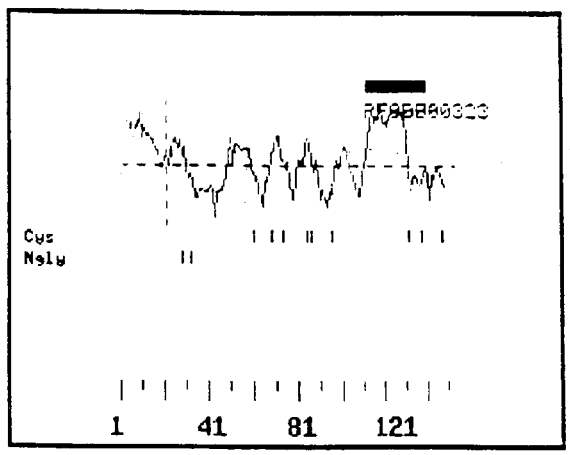
FIG. 2 depicts a hydropathy plot of a human ELVIS-1. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace. Below the hydropathy plot, the amino acid sequence of ELVIS-1 is depicted. The amino acid sequence of the signal sequence of ELVIS-1 is indicted by underlining and the letter "S" and amino acid sequence of the transmembrane domain of ELVIS-1 is indicated by underlining and a "TM".

The present invention is based, at least in part, on the discovery of cDNA molecules which encode a novel family of proteins having significant identity to transforming growth factor-α and epidermal growth factor, referred to herein as epidermal growth factor-like variant in skin proteins ("ELVIS" family or "ELVIS" proteins). Described herein are ELVIS-1 (SEQ ID NO:1), ELVIS-2 (SEQ ID NO:4) and ELVIS-3 (SEQ ID NO:7) nucleic acid molecules and the corresponding polypeptides which the nucleic acid molecules encode (SEQ ID NO:2, SEQ ID NO:5, and SEQ ID NO:8, respectively).

The ELVIS proteins and nucleic acid molecules comprise a family of molecules having certain conserved structural and functional features. As used herein, the term "family" is intended to mean two or more proteins or nucleic acid molecules having a common structural domain and having sufficient amino acid or nucleotide sequence identity as defined herein. Family members can be from either the same or different species. For example, a family can comprises two or more proteins of human origin, or can comprise one or more proteins of human origin and one or more of non-human origin. Members of the same family may also have common structural domains.

For example, the EGF/TGF-α family to which the ELVIS proteins of the invention bear significant sequence identity, are a family of mitogens which contain a conserved pattern of cysteine residues. Conserved cysteine residues, as used herein, refer to cysteine residues which are maintained within ELVIS family members (and/or EGF/TGF-α family members). This cysteine pattern is referred to herein as an epidermal growth factor (EGF) domain. These cysteine residues form disulfide bonds which can affect the structural integrity of the protein. Thus, included within the scope of the invention are ELVIS proteins having an EGF domain. As used herein, an EGF-domain refers to an amino acid sequence of about 25 to 50, preferably about 30 to 45, 30 to 40, and more preferably about 35, 36 to 40 amino acids in length. An EGF domain further contains at least about 2 to 10, preferably, 3 to 9, 4 to 8, or 6 to 7 conserved cysteine residues. The EGF domain of ELVIS-1 extends from about amino acid 60 to amino acid 95 of SEQ ID NO:2 (SEQ ID NO:15); the EGF domain of ELVIS-2 extends from about amino acid 51 to amino acid 87 of SEQ ID NO:5 (SEQ ID NO:16); the EGF domain of ELVIS-3 extends from about amino acid 51 to amino acid 86 of SEQ ID NO:8 (SEQ ID NO:17). By alignment of the amino acid sequence of TGF-α with the amino acid sequences of ELVIS-1, ELVIS-2 and ELVIS-3, conserved cysteine residues can be found. For example, there is a conserved cysteine residue at amino acid 47 of human TGF-α (SEQ ID NO:13) that corresponds to cysteine residue at amino acid 60 of ELVIS-1 (SEQ ID NO:2), at amino acid 51 of ELVIS-2 (SEQ ID NO:5), and at amino acid 51 of ELVIS-3 (SEQ ID NO:8); there is a conserved cysteine residue at amino acid 55 of human TGF-α (SEQ ID NO:13) that corresponds to a cysteine residue at amino acid 68 of ELVIS-1 (SEQ ID NO:2), at amino acid 59 of ELVIS-2 (SEQ ID NO:5), and at amino acid 59 of ELVIS-3 (SEQ ID NO:8); there is a conserved cysteine residue at amino acid 60 of human TGF-α (SEQ ID NO:13) that corresponds to a cysteine residue at amino acid 73 of ELVIS-1 (SEQ ID NO:2), at amino acid 64 of ELVIS-2 (SEQ ID NO:5), and amino acid 64 of ELVIS-3 (SEQ ID NO:8); there is a conserved cysteine residue at amino acid 71 of human TGF-α (SEQ ID NO:13) that corresponds to a cysteine residue at amino acid 84 of ELVIS-1 (SEQ ID NO:2), at amino acid 75 of ELVIS-2 (SEQ ID NO:5), and at amino acid 75 of ELVIS-3 (SEQ ID NO:8); there is a conserved cysteine residue at amino acid 73 of human TGF-α (SEQ ID NO:13) that corresponds to a cysteine residue at amino acid 86 of ELVIS-1 (SEQ ID NO:2), at amino acid 77 of ELVIS-2 (SEQ ID NO:5), and at amino acid 77 of ELVIS-3 (SEQ ID NO:8); and/or there is a conserved cysteine residue at amino acid 82 of human TGF-α (SEQ ID NO:13) that corresponds to a cysteine residue at amino acid 95 of ELVIS-1 (SEQ ID NO:2), at amino acid 87 of ELVIS-2 (SEQ ID NO:5), and at amino acid 86 of ELVIS-3 (SEQ ID NO:8).

Also included within the scope of the present invention are ELVIS proteins having a signal sequence. As used herein, a "signal sequence" includes a peptide of at least about 20 amino acid residues in length which occurs at the N-terminus of secretory and membrane-bound proteins and which contains at least about 70% hydrophobic amino acid residues such as alanine, leucine, isoleucine, phenylalanine, proline, tyrosine, tryptophan, or valine. In a preferred embodiment, a signal sequence contains at least about 15 to 25 amino acid residues, preferably about 18-22 amino acid residues, and has at least about 60-80%, more preferably 65-75%, and more preferably at least about 70% hydrophobic residues. A signal sequence serves to direct a protein containing such a sequence to a lipid bilayer. Thus, in one embodiment, an ELVIS protein contains a signal sequence of about amino acids 1 to 20 of SEQ ID NO:2, SEQ ID NO:5, or SEQ ID NO:8. The signal sequence is cleaved during processing of the mature protein.

The present invention also includes ELVIS proteins having a transmembrane domain. As used herein, a "transmembrane domain" refers to an amino acid sequence having at least about 20 to 25 amino acid residues in length and which contains at least about 65-70% hydrophobic amino acid residues such as alanine, leucine, isoleucine, phenylalanine, proline, tyrosine, tryptophan, or valine. In a preferred embodiment, a transmembrane domain contains at least about 15 to 30 amino acid residues, preferably about 20-25 amino acid residues, and has at least about 60-80%, more preferably 65-75%, and more preferably at least about 70% hydrophobic residues. An example of a transmembrane domain includes from about amino acids 111 to 133 of SEQ ID NO:2.

In one embodiment, an ELVIS protein of the invention includes an EGF domain, a signal sequence and is secreted. In another embodiment, an ELVIS protein of the invention includes an EGF domain, a transmembrane domain and is a membrane bound protein. In yet another embodiment, an ELVIS protein of the invention includes an EGF-domain, a signal sequence and a transmembrane domain.

Various features of human ELVIS-1, ELVIS-2 and ELVIS-3 are summarized below.

Human ELVIS-1

A cDNA encoding human ELVIS-1 was identified by screening a human keratinocyte library. Briefly, a cDNA library was prepared using cDNA prepared from RNA extracted from a human keratinocyte library and directionally cloned. ESTs were then generated from the 5' end. Clones were selected based on homology to TGF-α determined by BlastX screening.

One such clone, comprising human ELVIS-1, was identified. ELVIS-1 includes a 1858 nucleotide cDNA (FIG. 1; SEQ ID NO:1). The open reading frame of this cDNA, nucleotides 31 to 492 (SEQ ID NO:3), encodes a 154 amino acid putative membrane protein (FIG. 1; SEQ ID NO:2).

The signal peptide prediction program SIGNALP (Nielsen et al. (1997) *Protein Engineering* 10:1-6) predicted that human ELVIS-1 includes a 20 amino acid signal peptide (amino acid 1 to about amino acid 20 of SEQ ID NO:2) preceding the mature ELVIS-1 protein (corresponding to about amino acid 21 to amino acid 154 of SEQ ID NO:2; SEQ ID NO:18). Human ELVIS-1 includes an extracellular domain (amino acids 21-110 of SEQ ID NO:2; SEQ ID NO:12), a transmembrane (TM) domain (amino acids 111 to 133 of SEQ ID NO:2; SEQ ID NO:11); and a cytoplasmic domain (amino acids 134 to 154 of SEQ ID NO:2; SEQ ID NO:10).

The extracellular region of human ELVIS-1 includes an EGF-domain (about amino acids 60-95 of SEQ ID NO:2; SEQ ID NO:15).

A clone, Epjth095d12, which encodes human ELVIS-1 was deposited with the American Type Culture Collection (ATCC, 10801 University Boulevard, Manassas, Va. 20110-2209) on Nov. 11, 1998 and assigned Accession Number 98981. This deposit will be maintained under the terns of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

FIG. 2 depicts a hydropathy plot of human ELVIS-1. Relatively hydrophobic residues are above the horizontal line, and relatively hydrophilic residues are below the horizontal line. As shown in the hydropathy plot, the hydrophobic region at the beginning of the plot which corresponds to about amino acids 1 to 20 of SEQ ID NO:2 is the signal sequence of ELVIS-1. In addition, the hyrdophobic region in the middle of the plot which corresponds to about amino acids 111 to 133 of SEQ ID NO:2 is the transmembrane domain of ELVIS-1. The cysteine residues (cys) and potential N-glycosylation sites (Ngly) are indicated by short vertical lines just below the hydropathy trace.

The amino acid sequence of human ELVIS-1 (SEQ ID NO:2) was used to search public databases (using BLASTP; Altschul et al. (1990) *J. Mol. Biol.* 215:403-410) in order to identify proteins having homology to human ELVIS-1. This analysis revealed that human ELVIS-1 has considerable homology to various species of TGF-α including, for-example, mouse, rat, pig, sheep TGF-α. FIG. 7 depicts an alignment of the amino acids sequences of human ELVIS-1, and human TGF-α (SEQ ID NO:13) which have 24.4% sequence identity.

Human ELVIS-2

Two additional clones having significant homology to human ELVIS-1 and TGF-α were identified by the screening method described above. Both of these clones were sequenced and found to be splice variants of ELVIS-1. The first variant is referred to herein as ELVIS-2. The human ELVIS-2 cDNA (FIG. 3; SEQ ID NO:4) includes an open reading frame (nucleotides 15 to 323 of SEQ ID NO:4; SEQ ID NO:6) encoding a 103 amino acid putative secreted protein (FIG. 3; SEQ ID NO:5). The signal peptide prediction program SIGNALP (Nielsen et al. (1997) *Protein Engineering* 10:1-6) predicted that human ELVIS-2 includes a 20 amino acid signal peptide (amino acid 1 to about amino acid 20 of SEQ ID NO:5) preceding the mature protein (about amino acid 21 to amino acid 103 of SEQ ID NO:5; SEQ ID NO:19). Human ELVIS-2 also includes an EGF domain (about amino acids 51 to 87 of SEQ ID NO:5; SEQ ID NO:16).

A clone, Epjthkf037e06, which encodes human ELVIS-1 was deposited with the American Type Culture Collection (ATCC, 10801 University Boulevard, Manassas, Va. 20110-2209) on Nov. 11, 1998 and assigned Accession Number 98982. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Figure 4:
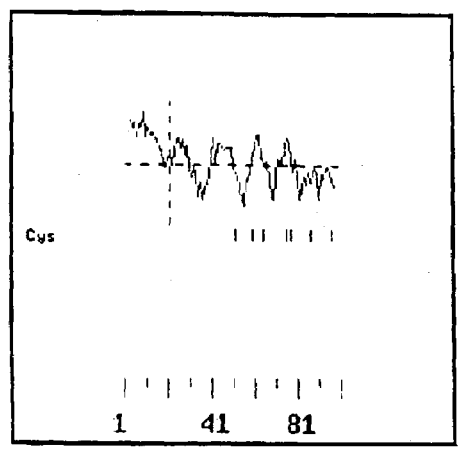
FIG. 4 depicts a hydropathy plot of human ELVIS-2. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace. Below the hydropathy plot, the amino acid sequence of ELVIS-2 is depicted and the signal sequence of ELVIS-2 is indicted by underlining and the letter "S".

FIG. 4 depicts a hydropathy plot of the splice variant ELVIS-2. Relatively hydrophobic residues are above the horizontal line, and relatively hydrophilic residues are below the horizontal line. As shown in the hydropathy plot, the hydrophobic region at the beginning of the plot which corresponds to about amino acids 1 to 20 of SEQ ID NO:5 is the signal sequence of ELVIS-2. The cysteine residues (cys) and potential N-glycosylation sites (Ngly) are indicated by short vertical lines just below the hydropathy trace.

Human ELVIS-3

The second clone having significant homology to ELVIS-1 and TGF-α is a splice variant of ELVIS-1 referred to herein as ELVIS-3. The human ELVIS-3 cDNA (FIG. 5; SEQ ID NO:7) includes an open reading frame (nucleotides 12 to 294 of SEQ ID NO:7; SEQ ID NO:9) encoding a 94 amino acid putative secreted protein (FIG. 3; SEQ ID NO:8). The signal peptide prediction program SIGNALP (Nielsen et al. (1997) *Protein Engineering* 10:1-6) predicted that human ELVIS-3 includes a 20 amino acid signal peptide (amino acid 1 to about amino acid 20 of SEQ ID NO:8) preceding the mature protein (about amino acid 21 to amino acid 94 of SEQ ID NO:8; SEQ ID NO:20).

Human ELVIS-3 also includes an EGF domain (about amino acids 51 to 86 of SEQ ID NO:8; SEQ ID NO:17).

A clone, Epjthkf064b08, which encodes human ELVIS-3 was deposited with the American Type Culture Collection (ATCC, 10801 University Boulevard, Manassas, Va. 20110-2209) on Nov. 11, 1998 and assigned Accession Number 98983. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Figure 6:
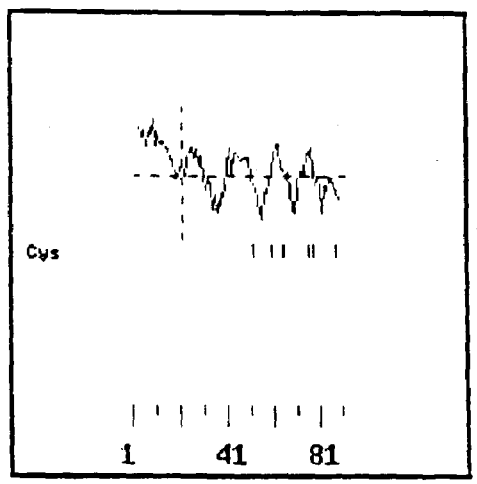
FIG. 6 depicts a hydropathy plot of human ELVIS-3, another variant of ELVIS-1. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace. Below the hydropathy plot, the amino acid sequence of ELVIS-3 is depicted and the signal sequence of ELVIS-3 is indicted by underlining and the letter "S".

FIG. 6 depicts a hydropathy plot of splice variant ELVIS-3. Relatively hydrophobic residues are above the horizontal line, and relatively hydrophilic residues are below the horizontal line. As shown in the hydropathy plot, the hydrophobic region at the beginning of the plot which corresponds to about amino acids 1 to 20 of SEQ ID NO:8 is the signal sequence of ELVIS-3. The cysteine residues (cys) and potential N-glycosylation sites (Ngly) are indicated by short vertical lines just below the hydropathy trace.

Additional sequencing analysis of the ELVIS-3 cDNA clone described above provided the cDNA sequence shown in FIG. 9 (SEQ ID NO:21).

Comparison of ELVIS-1, ELVIS-2 and ELVIS-3

An alignment of the amino acid sequences of human ELVIS-1 (SEQ ID NO:2), ELVIS-2 (SEQ ID NO:5) and ELVIS-3 (SEQ ID NO:8) is shown in FIG. 8. The alignment was performed using the Clustal algorithm which is part of the MEGALIGN program. The multiple alignment parameters are as follows: a PAM250 scoring matrix; Gap Penalty=10; Gap Extension Penalty=0.05. Elvis-1 is 67% identical to ELVIS-2 and 61% identical to ELVIS-3, while ELVIS-2 and ELVIS-3 are 91.3% identical.

This alignment shows that ELVIS-1 has a signal sequence from amino acids 1 to 20 of SEQ ID NO:2, which is identical to the signal sequences of ELVIS-2 (amino acids 1 to 20 of SEQ ID NO:5) and ELVIS-3 (amino acids 1 to 20 of SEQ ID NO:8). In addition, this alignment shows that ELVIS-1 has an extracellular domain, a transmembrane domain and a cytoplasmic domain, whereas both ELVIS-2 and ELVIS-3 lack a transmembrane domain and a cytoplasmic domain, thus leading to the conclusion that ELVIS-2 and ELVIS-3 are wholly secreted forms of ELVIS-1, which is itself a membrane-bound protein.

Antibodies Directed Against ELVIS

The following peptides were used to generate polyclonal antibodies in rabbits by standard techniques: LCLEDHN-SYCING (SEQ ID NO:22), GYTGERCEHLTLT (SEQ ID NO:23) and LKSPYNVCSGERRPL (SEQ ID NO:24).

Expression of ELVIS-1 Increases the Growth Rate of Fibroblasts

Retroviral expression vectors capable of expressing either ELVIS-1 or ELVIS-2 were generated using the MSCVpuro retrovirus vector. The resulting ELVIS-1 and ELVIS-2 retroviral expression vectors were used produce retrovirus for infection of NIH3T3 fibroblasts to generate ELVIS-1 expressing fibroblasts and ELVIS-2 expressing fibroblasts. Infected cells were grown for eight days under puromycin selection. The growth rate of ELVIS-1 expressing fibroblasts, ELVIS-2 expressing fibroblasts, and control fibroblasts was measured by thymidine incorporation as follows. Cells were plated at various densities in 96 well plates. After 24 hours, 1 μC of $H^3$-tymidine was added to each well. After 6 hours of labeling, the cells were harvested and the level of incorporated $H^3$-tymidine was measured.

This analysis revealed fibroblasts expressing ELVIS-1 grow about twice as quickly as control fibroblasts.

ELVIS-2 Stimulates the Growth and Differentiation of Keratinocytes

The effect of ELVIS-2 on the growth and differentiation of keritinocytes was examined as follows. In a first experiment, approximately 50,000 human fetal keritinocytes (strain YF29) were plated on irradiated NIH3T3 cells in cFAD medium with various combinations of TGF-α and recombinant ELVIS-2. The cells were fed every three days. On day 10 the cells were fixed in formaldehyde, stained with rhodamine B and examined. Cells cultured in the presence of ELVIS-2 piled up into epithelial layers rather than growing spread out on the plate. Cells cultured in the presence of 100 ng/mL ELVIS-2 formed raised "blisters" of cells. In a second experiment, approximately 20 human fetal keritinocytes (strain YF29) were plated on irradiated NIH3T3 cells in cFAD medium. Six days later, TGF-α and/or ELVIS-2 was added to the cultures. The cells were fed every 4 days. On day 16, the cells were fixed in formaldehyde, stained with rhodamine B, and examined. This experiment revealed that exposure to ELVIS-2 induces "blister" formation in the cell culture in both the presence and absence of TGF-α. The inducement of blister formation by ELVIS-2 suggests that ELVIS may stimulate the growth and differentiation of keratinocytes.

ELVIS-2 and ELVIS-3 are Wholly Secreted Proteins

A secretion analysis assay revealed that both ELVIS-2 and ELVIS-3 are secreted into the medium.

Chromosomal Location of ELVIS

Genomic mapping of ELVIS revealed that ELVIS maps to chromosomal location 4q12-13.

Northern Blot Analysis of ELVIS Expression

Northern blot analysis of ELVIS expression revealed expression in keratinocytes and HeLa cells.

In situ Analysis of ELVIS Expression

Expression of ELVIS in situ was analyzed using two probes, one to the coding region of ELVIS and one to the 3' UTR of ELVIS. This analysis revealed that ELVIS is expressed in stratified squamous epithelium within the cervix. No expression was observed in human skin, monkey skin, human esophagus, or human tonsil.

ELVIS as an Agonist or Antagonist of EGF

ELVIS and modulators of the expression or activity of ELVIS may act as agonists or antagonists of EGF. Such molecules may increase or decrease the activity of the EGF receptor, the erbB2 (HER-2) receptor, the erbB3 (HER-3) receptor, and/or the erbB4 (HER-4) receptor. The effect of ELVIS and modulators of the expression or activity of ELVIS on these receptors can be examined using cells that express one or more of these receptors. For example, A431cells (ATCC CRL-1555) over express EGF receptor; SKOV-3 cells (ATCC HTB-77) express erbB2; SKBR-3 cells (ATCC HTB-30) express EGF receptors, erbB2 and erbB3; and MDA MB-453 cells (ATCC HTB-131) express erbB2, erbB3 and erbB4. The cells are grown in standard medium (e.g., DMEM with 10% fetal calf serum) in the presence or absence of EGF, TGF-α, or neuregulin and an ELVIS polypeptide (e.g., the extracellular domain of ELVIS-1) or a modulator of the expression or activity of ELVIS. The activity of the receptor(s) expressed by the cells can be measured directly using an anti-phosphotyrosine antibody or indirectly using a standard cell proliferation assay.

For example, MDA-MB453, SKBR-3 and SKOV-3 cells are grown to 80% confluency in DMEM supplemented with 10% FCS in a humidified atmosphere of 5% CO2 at 37° C. The cells are then replated in serum-free media for 16 h before being exposed to NDF (100 ng/mL), EGF (100 ng/mL) or various concentrations of ELVIS for 15 min at 37° C. Cell lysates are prepared and comparable amounts of protein separated on a 10% SDS PAGE gel. Following transfer to nitrocellulose, immunodetection of phosphorylated proteins is performed using the monoclonal antiphosphotyrosine antibody 4G10 (Upstate Biotechnology, NY) as described by the manufacturer and utilizing ECL (Amersham). NDF and EGF can be purchased from R&D Systems (Minneapolis, Minn.). For immunoprecipitation assays 1 mg of cell extract is incubated with antibodies to erbB4, EGFR, ErbB3 or erbB2(Santa Cruz, Calif.) at a concentration of 1 mg/ml for 2 h at 4° C. Samples are then bound to protein G agarose for 12 h at 4° C., before being washed 4 times in lysis buffer. Immunoprecipitated samples are resuspended in sample buffer, boiled for 5' and then electrophoresed through SDS PAGE gels. Gels are then transferred and blotted as detailed above.

TABLE 1

Summary of Human ELVIS-1, ELVIS-2 and ELVIS-3 Sequence Information

| Gene | cDNA | ORF | Protein | FIG. | Accession No. |
| --- | --- | --- | --- | --- | --- |
| HUMAN ELVIS-1 | SEQ ID NO:1 | SEQ ID NO:3 | SEQ ID NO:2 | FIG. 1 | 98981 |
| HUMAN ELVIS-2 | SEQ ID NO:4 | SEQ ID NO:6 | SEQ ID NO:5 | FIG. 3 | 98982 |
| HUMAN ELVIS-3 | SEQ ID NO:7 SEQ ID NO:21 | SEQ ID NO:9 | SEQ ID NO:8 | FIG. 5 | 98983 |

TABLE 2

Summary of Domains of Human ELVIS-1, ELVIS-2 and ELVIS-3 Proteins

| Protein | Signal Sequence | Mature Protein | Extracellular Domain | Transmembrane Domain | Cytoplasmic Domain |
| --- | --- | --- | --- | --- | --- |
| HUMAN ELVIS-1 | aa 1–20 | aa 21–644 | aa 21–110 | aa 111–133 | aa 133–154 |
| SEQ ID NO:2 | SEQ ID NO:14 | SEQ ID NO:18 | SEQ ID NO:12 | SEQ ID NO:11 | SEQ ID NO:10 |

TABLE 2-continued

Summary of Domains of Human ELVIS-1, ELVIS-2 and ELVIS-3 Proteins

| Protein | Signal Sequence | Mature Protein | Extracellular Domain | Transmembrane Domain | Cytoplasmic Domain |
|---|---|---|---|---|---|
| HUMAN ELVIS-2 SEQ ID NO:5 | aa 1–20 SEQ ID NO:14 | aa 21–103 SEQ ID NO:19 | | | |
| HUMAN ELVIS-3 SEQ ID NO:8 | aa 1–20 SEQ ID NO:14 | aa 21–94 SEQ ID NO:20 | | | |

Use of ELVIS Nucleic Acids, Polypeptides, and ELVIS Agonists or Antagonists

The ELVIS proteins of the invention comprise a family of proteins with significant identity to TGF-α which is a member of the EGF/TGF-α family of proteins. Other members of the EGF/TGF-α family, including amphiregulin, heparin-binding EGF (HB-EGF), and betacellulin, have been identified based on sequence similarity, mitogenic activity and the capacity to interact with the EGF-receptor. Based on the sequence similarity between the ELVIS proteins and TGF-α, ELVIS proteins likely function in a similar manner as members of the EGF/TGF-α family. Thus, ELVIS modulators can be used to treat any EGF/TGF-α-associated disorders.

For example, the ELVIS proteins likely play a role in wound healing. In vitro studies have shown that EGF and TGF-α influence a number of cellular processes involved in soft tissue repair leading to their categorization as wound hormones for wound healing. For example, both EGF and TGF-α induce proliferation of dermal fibroblasts (Buckley-Sturrock et al. (1989) *J. Cell. Biol.* 138:70-78; Laato et al. (1987) *J. Biochem.* 247:385-388), EGF exerts proliferative and chemotaxis effects on granulation-tissue derived fibroblasts and induces collagenase and hyaluronic synthesis (Laato et al. (1988) *Acta. Chir. Scand. Suppl.* 546:4-44), and EGF stimulates keratinocyte proliferation and migration (Barrandon et al. (1987) *Cell* 50:1131-1137, Chernoff (1990) *Growth Factors* 11:235-257). TGF-α is also abundant in self renewing tissue such as skin and, thus can provide a mitogenic signal for self renewing cells.

Clinical trials with EGF have also demonstrated that EGF accelerates healing in burn patients receiving skin-grafts. Brown et al. (1989) *N. Engl. J. Med.* 321:76-79. The ELVIS nucleic acid molecule, proteins or modulators thereof of the invention likely affect various cells, e.g., various skin cells associated with wound healing. Effects that the ELVIS nucleic acid molecules, proteins, or modulators thereof have on various cells, e.g., skin cells, include proliferation and migration. As ELVIS-1 was isolated from a keratinocyte library, is expressed in keratinocytes, and is homologous to TGF-α, it likely plays a role in the proliferation and/or migration of keratinocytes. Accordingly, the ELVIS proteins, nucleic acids and/or modulators of the invention are useful for the treatment of wounds, e.g., burns.

In addition, the effects of the ELVIS proteins of the invention on various skin cells can have cosmetic applications. For example, the ELVIS proteins play a role in the proliferation and/or migration of skin cells such as hair follicles and, therefore, are useful for modulating (e.g., stimulating or promoting) hair growth. Accordingly, the ELVIS proteins, nucleic acids and/or modulators of the invention have cosmetic use such as for treatment of hair loss or the treatment of unwanted hair growth.

A number of different cancer cells exhibit elevated levels of EGF-receptors. Groenen et al. (1994) *Growth Factors* 11:235-257. Moreover, TGF-α has been associated with the growth and maintenance of tumors including those of the lung, breast, head and neck, prostate, brain, liver, bladder, endometrium, kidney and gastrointestinal tract. Oppenheim et al., eds., *Clinical Applications of Cytokines: Role in Pathogenesis, Diagnosis and Therapy* (Oxford University Press, New York, N.Y., 1993, pp 263-265). Experimental trials have begun with TGF-α toxins against EGF-receptor, e.g., TGF-α fused with *Pseudomonas* exotoxin (PE), diphtheria toxin (DT) or ricin, for treatment of cancer. In addition, antagonists of TGF-α are likely able to compete with autocrine TGF-α, and thus inhibit cancer growth.

The ELVIS nucleic acid molecules, proteins or modulators thereof also modulate cell proliferation, and thus are useful in modulating proliferative disorders such as cancer. Thus, ELVIS nucleic acid molecules, proteins or modulators thereof, e.g., antibodies, can be fused with a therapeutic moiety, e.g., toxin, or administered in combination with a theraepeutic moiety, e.g., PE, DT or ricin, to target receptors, e.g., EGF receptors, e.g., EGFr, HER-2, HER-3, or HER-4, on cancer cells, e.g., epithelial cancer cells (carcinoma cells), e.g., epithelial cells of the following tissues which have become cancerous: lung, breast, head and neck, prostate, liver, brain, bladder, cervix, endometrium, kidney, gastrointestinal tract, or ovary. In addition, modulators, e.g., antagonists, e.g., antibodies, of ELVIS, can be used to modulate, e.g., inhibit or reduce, aberrant ELVIS expression associated with, for example, proliferative disorders such as cancers. Accordingly, modulators of ELVIS activities, e.g., antagonists, as well as, ELVIS proteins used as targeting agents for toxins can be used for the treatment of proliferative disorders such as cancer.

Specifically, ELVIS proteins can play a role in the proliferation and migration of various skin cells. Thus, aberrant ELVIS expression and/or ELVIS activities can be involved in various skin proliferative disorders. Therefore, modulators of ELVIS expression and/or activities, e.g., ELVIS antagonists, can be useful in the treatment of skin proliferative disorders such as psoriasis. Modulators of ELVIS expression and/or activities, e.g., ELVIS antagonists, can be useful in the treatment of contact dermatitis.

It has been reported (Ginns et al. (1998)) that a locus, MHW1 (603663), on 4 p at D4S2949 is strongly linked with mental health wellness (e.g., absence of bipolar affective disorder) in Old Order Amish pedigrees. These findings were consistent with the hypothesis that certain alleles could prevent or modify the clinical manifestations of bipolar affective disorder and perhaps other related affective disorders. Thus, modulators of ELVIS expression or activity may be useful for treatment of bipolar affective disorder and other related affective disorders.

Various aspects of the invention are described in further detail in the following subsections.

I. Isolated Nucleic Acid Molecules

One aspect of the invention pertains to isolated nucleic acid molecules that encode a polypeptide of the invention or a biologically active portion thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, 3, 4, 6, 7, 9, or a complement thereof, can be isolated using standard molecular biology techniques and the sequence information provided herein. Using all or a portion of the nucleic acid sequences of SEQ ID NO:1, 3, 4, 6, 7 or 9 as a hybridization probe, nucleic acid molecules of the invention can be isolated using standard hybridization and cloning techniques (e.g., as described in Sambrook et al., eds., *Molecular Cloning: A Laboratory Manual*, 2nd ed., Cold Spring Harbor Laboratory, Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which is a complement of the nucleotide sequence of SEQ ID NO:1, 3, 4, 6, 7, or 9, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence encoding a full length polypeptide of the invention for example, a fragment which can be used as a probe or primer or a fragment encoding a biologically active portion of a polypeptide of the invention. The nucleotide sequence determined from the cloning one gene allows for the generation of probes and primers designed for use in identifying and/or cloning homologues in other cell types, e.g., from other tissues, as well as homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, 3, 4, 6, 7, or 9, or of a naturally occurring mutant of SEQ ID NO:1, 3, 4, 6, 7, or 9.

Probes based on the sequence of a nucleic acid molecule of the invention can be used to detect transcripts or genomic sequences encoding the same protein molecule encoded by a selected nucleic acid molecule. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

A nucleic acid fragment encoding a "biologically active portion" of a polypeptide of the invention can be prepared by isolating a portion of any of SEQ ID NOS:3, 6 or 9, expressing the encoded portion of the polypeptide protein (e.g., by recombinant expression in vitro) and assessing the activity of the encoded portion of the polypeptide.

The invention further encompasses nucleic acid molecules that differ from the nucleotide sequence of SEQ ID NO:1, 3, 4, 6, 7, or 9 due to degeneracy of the genetic code and thus encode the same protein as that encoded by the nucleotide sequence of SEQ ID NO:3, 6 or 9.

In addition to the nucleotide sequences of SEQ ID NOs:3, 6, and 9, it will be appreciated by those skilled in the art that DNA sequence polymorphisms that lead to changes in the amino acid sequence may exist within a population (e.g., the human population). Such genetic polymorphisms may exist among individuals within a population due to natural allelic variation. An allele is one of a group of genes which occur alternatively at a given genetic locus. As used herein, the phrase "allelic variant" refers to a nucleotide sequence which occurs at a given locus or to a polypeptide encoded by the nucleotide sequence. As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins of the invention from other species (homologues), which have a nucleotide sequence which differs from that of the human protein described herein are intended to be within the scope of the invention. Nucleic acid molecules corresponding to natural allelic variants and homologues of a cDNA of the invention can be isolated based on their identity to the human nucleic acid molecule disclosed herein using the human cDNAs, or a portion thereof, as a hybridization probe according to standard hybridization techniques under stringent hybridization conditions. For example, a cDNA encoding a soluble form of a membrane-bound protein of the invention isolated based on its hybridization to a nucleic acid molecule encoding all or part of the membrane-bound form. Likewise, a cDNA encoding a membrane-bound form can be isolated based on its hybridization to a nucleic acid molecule encoding all or part of the soluble form.

Accordingly, in another embodiment, an isolated nucleic acid molecule of the invention is at least 300 (325, 350, 375, 400, 425, 450, 500, 550, 600, 650, 700, 800, 900, 1000, or 1290) nucleotides in length and hybridizes under stringent conditions to the nucleic acid molecule comprising the nucleotide sequence, preferably the coding sequence, of SEQ ID NO:1, 3, 4, 6, 7, or 9, or a complement thereof.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to the sequence of SEQ ID NO:1, 3, 4, 6, 7, or 9, or a complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of a nucleic acid molecule of the invention sequence that may exist in the population, the skilled artisan will further appreciate that changes can be introduced by mutation thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologues of various species may be non-essential for activity and thus would be likely targets for alteration. Alternatively, amino acid residues that are conserved among the homologues of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:2, 5, or 8, yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2, 5, or 8.

An isolated nucleic acid molecule encoding a variant protein can be created by introducing one or more nucleotide substitutions, additions or deletions into the nucleotide sequence of SEQ ID NO:1, 3, 4, 6, 7, or 9 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In a preferred embodiment, a mutant polypeptide that is a variant of a polypeptide of the invention can be assayed for: (1) the ability to form protein:protein interactions with proteins in a signaling pathway of the polypeptide of the invention; (2) the ability to bind a ligand of the polypeptide of the invention; or (3) the ability to bind to an intracellular target protein of the polypeptide of the invention. In yet another preferred embodiment, the mutant polypeptide can be assayed for the ability to modulate cellular proliferation, cellular migration or chemotaxis, or cellular differentiation.

The present invention encompasses antisense nucleic acid molecules, i.e., molecules which are complementary to a sense nucleic acid encoding a polypeptide of the invention, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylamninomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res*. 15:6625-6641). The antisense nucleic acid molecule can also comprise a 2'-o-methylribonucleotide (Inoue et al. (1987) *Nucleic Acids Res*. 15:6131-6148) or a chimeric RNA-DNA analogue (Inoue et al. (1987) *FEBS Lett*. 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of the invention can be used to select a catalytic RNA having a specific ribonuclease activity from a pool of RNA molecules. See, e.g., Bartel and Szostak (1993) *Science* 261:1411-1418.

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des*. 6(6):569-84; Helene (1992) *Ann. N.Y. Acad. Sci*. 660:27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5-23). As used herein, the terms "peptide nucleic acids" or "PNAs" refer to nucleic acid mimics, e.g., DNA mimics, in which the deoxyribose-phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93: 14670-675.

PNAs can be used in therapeutic and diagnostic applications. For example, PNAs can be used as antisense; or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) *Proc. Natl. Acad. Sci. USA* 93: 14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) *Nucleic Acids Res.* 17:5973-88). PNA monomers are then coupled in a stepwise manner to produce a chimeric molecule with a 5' PNA segment and a 3' DNA segment (Finn et al. (1996) *Nucleic Acids Res.* 24(17):3357-63). Alternatively, chimeric molecules can be synthesized with a 5' DNA segment and a 3' PNA segment (Peterser et al. (1975) *Bioorganic Med. Chem. Lett.* 5:1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958-976) or intercalating agents (see, e.g., Zon (1988) *Pharm. Res.* 5:539-549). To this end, the oligonucleotide may be conjugated to another molecule, e.g., a peptide, hybridization triggered cross-linking agent, transport agent, hybridization-triggered cleavage agent, etc.

II. Isolated Proteins and Antibodies

One aspect of the invention pertains to isolated proteins, and biologically active portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide of the invention include polypeptides comprising amino acid sequences sufficiently identical to or derived from the amino acid sequence of the protein (e.g., the amino acid sequence shown in any of SEQ ID NOS:2, 5, or 8), which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence of SEQ ID NO:2, 5, or 8 Other useful proteins are substantially identical (e.g., at least about 45%, preferably 55%, 65%, 75%, 85%, 95%, or 99%) to any of SEQ ID NO:2, 5, or 8 and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. Id. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The invention also provides chimeric or fusion proteins. As used herein, a "chimeric protein" or "fusion protein" comprises all or part (preferably biologically active) of a polypeptide of the invention operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the N-terminus or C-terminus of the polypeptide of the invention. One useful fusion protein is a GST fusion protein in which the polypeptide of the invention is fused to the C-terminus of GST sequences. Such fusion proteins can facilitate the purification of a recombinant polypeptide of the invention.

In another embodiment, the fusion protein contains a heterologous signal sequence at its N-terminus. For example, the native signal sequence of a polypeptide of the invention can be removed and replaced with a signal sequence from another protein. For example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide of the invention is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction may be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence of a polypeptide of the invention (SEQ ID NO:14) can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to the signal sequence itself and to the polypeptide in the absence of the signal sequence. (i.e., the cleavage products). In one embodiment, a nucleic acid sequence encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

In another embodiment, the signal sequences of the present invention can be used to identify regulatory sequences, e.g., promoters, enhancers, repressors. Since signal sequences are the most amino-terminal sequences of a peptide, it is expected that the nucleic acids which flank the signal sequence on its amino-terminal side will be regulatory sequences which affect transcription. Thus, a nucleotide sequence which encodes all or a portion of a signal sequence can be used as a probe to identify and isolate signal sequences and their flanking regions, and these flanking regions can be studied to identify regulatory elements therein.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang (1983) *Tetrahedron* 39:3; Itakura et al. (1984) *Annu. Rev. Biochem*. 53:323; Itakura et al. (1984) *Science* 198: 1056; Ike et al. (1983) *Nucleic Acid Res*. 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) *Proc. Natl. Acad. Sci. USA* 89:7811-7815; Delgrave et al. (1993) *Protein Engineering* 6(3):327-331).

An isolated polypeptide of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30) amino acid residues of the amino acid sequence of SEQ ID NO:2, 5 or 8, and encompasses an epitope of the protein such that an antibody raised against the peptide forms a specific immune complex with the protein.

Preferred epitopes encompassed by the antigenic peptide are regions that are located on the surface of the protein, e.g., hydrophilic regions. FIGS. 2, 4 and 6 are hydrophobicity plots of the proteins of the invention. These plots or similar analyses can be used to identify hydrophilic regions.

An immunogen typically is used to prepare antibodies by immunizing a suitable subject, (e.g., rabbit, goat, mouse or other mammal). An appropriate immunogenic preparation can contain, for example, recombinantly expressed or chemically synthesized polypeptide. The preparation can further include an adjuvant, such as Freund's complete or incomplete adjuvant, or similar immunostimulatory agent.

Accordingly, another aspect of the invention pertains to antibodies directed against a polypeptide of the invention. The term "antibody" as used herein refers to immunoglobulin molecules and immunologically active portions of immunoglobulin molecules, i.e., molecules that contain an antigen binding site which specifically binds an antigen, such as a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$^2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing hybridomas is well known (see generally *Current Protocols in Immunology* (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod Hybridomas* 3:81-85; Huse et al. (1989) *Science* 246:1275-1281; Griffiths et al. (1993) *EMBO J.* 12:725-734.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope. (Jespers et al. (1994) *Bio/technology* 12:899-903).

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

Techniques for conjugating such therapeutic moiety to antibodies are well known, see, e.g., Arnon et al., "Monoclonal Antibodies for Immunotargeting of Drugs in Cancer Therapy", in Monoclonal Antibodies and Cancer Therapy, Reisfeld et al. (eds.), pp. 243-56 (Alan R. Liss, Inc. 1985); Hellstrom et al., "Antibodies for Drug Delivery", in Controlled Drug Delivery (2nd Ed.), Robinson et al. (eds.), pp. 623-53 (Marcel Dekker, Inc. 1987); Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985); "Analysis, Results, and Future Prospective of The Therapeutic Use of Radiolabeled Antibody In Cancer Therapy", in Monoclonal Antibodies for Cancer Detection and Therapy, Baldwin et al. (eds.), pp.303-16 (Academic Press 1985), and Thorpe et al., "The Preparation and Cytotoxic Properties of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

In addition, antibodies of the invention, either conjugated or not conjugated to a therapeutic moiety, can be administered together or in combination with a therapeutic moiety such as a cytotoxin, a therapeutic agent or a radioactive metal ion. The order of administration of the antibody and therapeutic moiety can vary. For example, in some embodiments, the antibody is administered concurrently (through the same or different delivery devices, e.g., syringes) with the therapeutic moiety. Alternatively, the antibody can be administered separately and prior to the therapeutic moiety. Still alternatively, the therapeutic moiety is administered separately and prior to the antibody. In many embodiments, these administration regimens will be continued for days, months or years.

III. Recombinant Expression Vectors and Host Cells

Another aspect of the invention pertains to vectors, preferably expression vectors, containing a nucleic acid encoding a polypeptide of the invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174

(DE3) from a resident γ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990)-119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res*. 20:2111-2118). Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari et al. (1987) *EMBO J*. 6:229-234), pMFa (Kurjan and Herskowitz, (1982) *Cell* 30:933-943), pJRY88 (Schultz et al. (1987) *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf9 cells) include the pAc series (Smith et al. (1983) *Mol. Cell Biol*. 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J*. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev*. 1:268-277), lymphoid-specific promoters (Calame and Eaton (1988) *Adv. Immunol*. 43:235-275), in particular promoters of T cell receptors (Winoto and Baltimore (1989) *EMBO J*. 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev*. 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (*Reviews—Trends in Genetics*, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride coprecipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce a polypeptide of the invention. Accordingly, the invention further provides methods for producing a polypeptide of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a sequences encoding a polypeptide of the invention have been introduced. Such host cells can then be used to create non-human transgenic animals in which exogenous sequences encoding a polypeptide of the invention have been introduced into their genome or homologous recombinant animals in which endogenous encoding a polypeptide of the invention sequences have been altered. Such animals are useful for studying the function and/or activity of the polypeptide and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding a polypeptide of the invention (or a homologue thereof) into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, 4,873, 191 and in Hogan, *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach*, Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication NOS. WO 97/07668 and WO 97/07669.

IV. Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more addtional active compounds.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). For example, polypeptides of the invention can to used to (i) modulate cellular proliferation; (ii) modulate cell migration and chemotaxis; (iii) modulate cellular differentiation; and/or (iv) modulate angiogenesis. The isolated nucleic acid molecules of the invention can be used to express proteins (e.g., via a recombinant expression vector in a host cell in gene therapy applications), to detect mRNA (e.g., in a biological sample) or a genetic lesion, and to modulate activity of a polypeptide of the invention. In addition, the polypeptides of the invention can be used to screen drugs or compounds which modulate activity or expression of a polypeptide of the invention as well as to treat disorders characterized by insufficient or excessive production of a protein of the invention or production of a form of a protein of the invention which has decreased or aberrant activity compared to the wild type protein. In addition, the antibodies of the invention can be used to detect and isolate a protein of the and modulate activity of a protein of the invention.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to polypeptide of the invention or have a stimulatory or inhibitory effect on, for example, expression or activity of a polypeptide of the invention.

In one embodiment, the invention provides assays for screening candidate or test compounds which bind to or modulate the activity of the membrane-bound form of a polypeptide of the invention or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des*. 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem*. 37:2678; Cho et al. (1993) *Science* 261:1303; Carrell et al. (1994) *Angew. Chem. Int. Ed. Engl*. 33:2059; Carell et al. (1994) *Angew. Chem. Int. Ed. Engl*. 33:2061; and Gallop et al. (1994) *J. Med. Chem*. 37:1233.

Libraries of compounds may be presented in solution (e.g., Houghten (1992) *Bio/Techniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865-1869) or phage (Scott and Smith (1990) *Science* 249:386-390; Devlin (1990) *Science* 249:404-406; Cwirla et al. (1990) *Proc. Natl. Acad. Sci. USA* 87:6378-6382; and Felici (1991) *J. Mol. Biol*. 222:301-310).

In one embodiment, an assay is a cell-based assay in which a cell which expresses a membrane-bound form of a polypeptide of the invention, or a biologically active portion thereof, on the cell surface is contacted with a test compound and the ability of the test compound to bind to the polypeptide determined. The cell, for example, can be a yeast cell or a cell of mammalian origin. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of a polypeptide of the invention, or a biologically active portion thereof, on the cell surface with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or a biologically active portion thereof as compared to the known compound.

In another embodiment, an assay is a cell-based assay comprising contacting a cell expressing a membrane-bound form of a polypeptide of the invention, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide protein to bind to or interact with a target molecule.

Determining the ability of a polypeptide of the invention to bind to or interact with a target molecule can be accomplished by one of the methods described above for determining direct binding. As used herein, a "target molecule" is a molecule with which a selected polypeptide (e.g., a polypeptide of the invention binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. A target molecule can be a polypeptide of the invention or some other polypeptide or protein. For example, a target molecule can be a component of a signal transduction pathway which facilitates transduction of an extracellular signal (e.g., a signal generated by binding of a compound to a polypeptide of the invention) through the cell membrane and into the cell or a second intercellular protein which has catalytic activity or a protein which facilitates the association of downstream signaling molecules with a polypeptide of the invention. Determining the ability of a polypeptide of the invention to bind to or interact with a target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g. luciferase), or detecting a cellular response, for example, cellular differentiation, or cell proliferation.

In yet another embodiment, an assay of the present invention is a cell-free assay comprising contacting a polypeptide of the invention or biologically active portion thereof with a test compound and determining the ability of the test compound to bind to the polypeptide or biologically active portion thereof. Binding of the test compound to the polypeptide can be determined either directly or indirectly as described above. In a preferred embodiment, the assay includes contacting the polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or biologically active portion thereof as compared to the known compound.

In another embodiment, an assay is a cell-free assay comprising contacting a polypeptide of the invention or biologically active portion thereof with a test compound and determining the ability of the test compound to modulate (e.g., stimulate or inhibit) the activity of the polypeptide or biologically active portion thereof. Determining the ability of the test compound to modulate the activity of the polypeptide can be accomplished, for example, by determining the ability of the polypeptide to bind to a target molecule by one of the methods described above for determining direct binding. In an alternative embodiment, determining the ability of the test compound to modulate the activity of the polypeptide can be accomplished by determining the ability of the polypeptide of the invention to further modulate the target molecule. For example, the catalytic/enzymatic activity of the target molecule on an appropriate substrate can be determined as previously described.

In yet another embodiment, the cell-free assay comprises contacting a polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the polypeptide to preferentially bind to or modulate the activity of a target molecule.

The cell-free assays of the present invention are amenable to use of both a soluble form or the membrane-bound form of a polypeptide of the invention. In the case of cell-free assays comprising the membrane-bound form of the polypeptide, it may be desirable to utilize a solubilizing agent such that the membrane-bound form of the polypeptide is maintained in solution. Examples of such solubilizing agents include non-ionic detergents such as n-octylglucoside, n-dodecylglucoside, n-octylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy -1-propane sulfonate (CHAPSO), or N-dodecyl=N,N-dimethyl -3-ammonio -1-propane sulfonate.

In more than one embodiment of the above assay methods of the present invention, it may be desirable to immobilize either the polypeptide of the invention or its target molecule to facilitate separation of complexed from uncomplexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or A polypeptide of the invention, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the polypeptide of the invention or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the polypeptide of the invention or target molecules but which do not interfere with binding of the polypeptide of the invention to its target molecule can be derivatized to the wells of the plate, and unbound target or polypeptidede of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a polypeptide of the invention are identified in a method in which a cell is contacted with a candidate compound and the expression of the selected mRNA or protein (i.e., the mRNA or protein corresponding to a polypeptide or nucleic acid of the invention) in the cell is determined. The level of expression of the selected mRNA or protein in the presence of the candidate compound is compared to the level of expression of the selected mRNA or protein in the absence of the candidate compound. The candidate compound can then be identified as a modulator of expression of the polypeptide of the invention based on this comparison. For example, when expression of the selected mRNA or protein is greater (statistically significantly greater) in the presence of the candidate compound than in its absence, the candidate compound is identified as a stimulator of the selected mRNA or protein expression. Alternatively, when expression of the selected mRNA or protein is less (statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a polypeptide of the inventions can be used as "bait proteins" in a two-hybrid assay or three hybrid assay (see, e.g., U.S. Pat. No. 5,283, 317; Zervos et al. (1993) *Cell* 72:223-232; Madura et al. (1993) *J. Biol. Chem*. 268:12046-12054; Bartel et al. (1993) *Bio/Techniques* 14:920-924; Iwabuchi et al. (1993) *Oncogene* 8:1693-1696; and PCT Publication No. WO 94/10300), to identify other proteins, which bind to or interact with the polypeptide of the invention and modulate activity of the polypeptide of the invention. Such binding proteins are also likely to be involved in the propagation of signals by the polypeptide of the inventions as, for example, upstream or downstream elements of a signaling pathway involving the polypeptide of the invention.

This invention further pertains to novel agents identified by the above-described screening assays and uses thereof for treatments as described herein.

B. Detection Assays

Portions or fragments of the cDNA sequences identified herein (and the corresponding a complete gene sequences) can be used in numerous ways as polynucleotide reagents. For example, these sequences can be used to: (i) map their respective genes on a chromosome and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a-portion of the sequence) of a gene has been isolated, this sequence can be used to map the location of the gene on a chromosome. Accordingly, nucleic acid molecules described herein or fragments thereof, can be used to map the location of the corresponding genes on a chromosome. The mapping of the sequences to chromosomes is an important first step in correlating these sequences with genes associated with disease.

Briefly, genes can be mapped to chromosomes by preparing PCR primers (preferably 15-25 bp in length) from the sequence of a gene of the invention. Computer analysis of the sequence of a gene of the invention can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the gene sequences will yield an amplified fragment. For a review of this technique, see D'Eustachio et al. ((1983) *Science* 220:919-924).

PCR mapping of somatic cell hybrids is a rapid procedure for assigning a particular sequence to a particular chromosome. Three or more sequences can be assigned per day using a single thermal cycler. Using the nucleic acid sequences of the invention to design oligonucleotide primers, sublocalization can be achieved with panels of fragments from specific chromosomes. Other mapping strategies which can similarly be used to map a gene to its chromosome include in situ hybridization (described in Fan et al. (1990) *Proc. Natl. Acad Sci. USA* 87:6223-27), pre-screening with labeled flow-sorted chromosomes, and pre-selection by hybridization to chromosome specific cDNA libraries. Fluorescence in situ hybridization (FISH) of a DNA sequence to a metaphase chromosomal spread can further be used to provide a precise chromosomal location in one step. For a review of this technique, see Verma et al. (Human Chromosomes: A Manual of Basic Techniques (Pergamnon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature 325:783-787.

Moreover, differences in the DNA sequences between individuals affected and unaffected with a disease associated with a gene of the invention can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The nucleic acid sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base. DNA sequence of selected portions of an individual's genome. Thus, the nucleic acid sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The nucleic acid sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, 4 or 7 can comfortably provide positive individual identification with a panel of perhaps 10 to 1,000 primers which each yield a noncoding amplified sequence of 100 bases. If predicted coding sequences, such as those in SEQ ID NO:3, 6 or 9 are used, a more appropriate number of primers for positive individual identification would be 500-2,000.

If a panel of reagents from the nucleic acid sequences described herein is used to generate a unique identification database for an individual, those same reagents can later be used to identify tissue from that individual. Using the unique identification database, positive identification of the individual, living or dead, can be made from extremely small tissue samples.

3. Use of Partial Gene Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the nucleic acid sequences of the invention or portions thereof, e.g., fragments derived from noncoding regions having a length of at least 20 or 30 bases.

The nucleic acid sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such probes can be used to identify tissue by species and/or by organ type.

C. Predictive Medicine

The present invention also pertains to the field of predictive medicine in which diagnostic assays, prognostic assays, pharmacogenomics, and monitoring clinical trails, are used for prognostic (predictive) purposes to thereby treat an individual prophylactically. Accordingly, one aspect of the present invention relates to diagnostic assays for determining expression of a polypeptide or nucleic acid of the invention and/or activity of a polypeptide of the invention, in the context of a biological sample (e.g., blood, serum, cells, tissue) to thereby determine whether an individual is afflicted with a disease or disorder, or is at risk of developing a disorder, associated with aberrant expression or activity of a polypeptide of the invention. The invention also provides for prognostic (or predictive) assays for determining whether an individual is at risk of developing a disorder associated with aberrant expression or activity of a polypeptide of the invention. For example, mutations in a gene of the invention can be assayed in a biological sample. Such assays can be used for prognostic or predictive purpose to thereby prophylactically treat an individual prior to the onset of a disorder characterized by or associated with aberrant expression or activity of a polypeptide of the invention.

Another aspect of the invention provides methods for expression of a nucleic acid or polypeptide of the invention or activity of a polypeptide of the invention in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Yet another aspect of the invention pertains to monitoring the influence of agents (e.g., drugs or other compounds) on the expression or activity of a polypeptide of the invention in clinical trials. These and other agents are described in further detail in the following sections.

1. Diagnostic Assays

An exemplary method for detecting the presence or absence of a polypeptide or nucleic acid of the invention in a biological sample involves obtaining a biological sample from a test subject and contacting the biological sample with a compound or an agent capable of detecting a polypeptide or nucleic acid (e.g., mRNA, genomic DNA) of the invention such that the presence of a polypeptide or nucleic acid of the invention is detected in the biological sample. A preferred agent for detecting mRNA or genomic DNA encoding a polypeptide of the invention is a labeled nucleic acid probe capable of hybridizing to mRNA or genomic DNA encoding a polypeptide of the invention. The nucleic acid probe can be, for example, a full-length cDNA, such as the nucleic acid of SEQ ID NO:1, 3, 4, 6, 7 or 9, or a portion thereof, such as an oligonucleotide of at least 15, 30, 50, 100, 250 or 500 nucleotides in length and sufficient to specifically hybridize under stringent conditions to a mRNA or genomic DNA encoding a polypeptide of the invention. Other suitable probes for use in the diagnostic assays of the invention are described herein.

A preferred agent for detecting a polypeptide of the invention is an antibody capable of binding to a polypeptide of the invention, preferably an antibody with a detectable label. Antibodies can be polyclonal, or more preferably, monoclonal. An intact antibody, or a fragment thereof (e.g., Fab or F(ab')$^2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of a polypeptide of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide of the invention include introducing into a subject a labeled antibody directed against the polypeptide. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a polypeptide of the invention or mRNA or genomic DNA encoding a polypeptide of the invention, such that the presence of the polypeptide or mRNA or genomic DNA encoding the polypeptide is detected in the biological sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention (e.g., a proliferative disorder, e.g., psoriasis or cancer). For example, the kit can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits may also include instructions for observing that the tested subject is suffering from or is at risk of developing a disorder associated with aberrant expression of the polypeptide if the amount of the polypeptide or mRNA encoding the polypeptide is above or below a normal level.

For antibody-based kits, the kit may comprise, for example: (1) a first antibody (e.g., attached to a solid support) which binds to a polypeptide of the invention; and, optionally, (2) a second, different antibody which binds to either the polypeptide or the first antibody and is conjugated to a detectable agent.

For oligonucleotide-based kits, the kit may comprise, for example: (1) an oligonucleotide, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention. The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

2. Prognostic Assays

The methods described herein can furthermore be utilized as diagnostic or prognostic assays to identify subjects having or at risk of developing a disease or disorder associated with aberrant expression or activity of a polypeptide of the invention. For example, the assays described herein, such as the preceding diagnostic assays or the following assays, can be utilized to identify a subject having or at risk of developing a disorder associated with aberrant expression or activity of a polypeptide of the invention, e.g., a proliferative disorder, e.g., psoriasis or cancer, or an angiogenic disorder. Alternatively, the prognostic assays can be utilized to identify a subject having or at risk for developing such a disease or disorder. Thus, the present invention provides a method in which a test sample is obtained from a subject and a polypeptide or nucleic acid (e.g., mRNA, genomic DNA) of the invention is detected, wherein the presence of the polypeptide or nucleic acid is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a polypeptide of the invention. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a polypeptide of the invention in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

The methods of the invention can also be used to detect genetic lesions or mutations in a gene of the invention, thereby determining if a subject with the lesioned gene is at risk for a disorder characterized aberrant expression or activity of a polypeptide of the invention. In preferred embodiments, the methods include detecting, in a sample of cells from the subject, the presence or absence of a genetic lesion or mutation characterized by at least one of an alteration affecting the integrity of a gene encoding the polypeptide of the invention, or the mis-expression of the gene encoding the polypeptide of the invention. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in a gene (see, e.g., Abravaya et al. (1995) *Nucleic Acids Res.* 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874-1878), transcriptional amplification system (Kwoh, et al. (1989) *Proc. Natl. Acad. Sci. USA* 86:1173-1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotides probes (Cronin et al. (1996) *Human Mutation* 7:244-255; Kozal et al. (1996) *Nature Medicine* 2:753-759). For example, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr*. 36:127-162; and Griffin et al. (1993) *Appl. Biochem. Biotechnol*. 38:147-159).

Other methods for detecting mutations in a selected gene include methods in which protection from cleavage agents is used to detect mismatched bases in RNA/RNA or RNA/DNA heteroduplexes (Myers et al. (1985) *Science* 230: 1242). In general, the technique of "mismatch cleavage" entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to basepair mismatches between the control and sample strands. RNA/DNA duplexes can be treated with RNase to digest mismatched regions, and DNA/DNA hybrids can be treated with S1 nuclease to digest mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) *Proc. Natl. Acad. Sci. USA* 85:4397; Saleeba et al. (1992) *Methods Enzymol*. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a selected sequence, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) *Proc. Natl. Acad. Sci. USA* 86:2766; see also Cotton (1993) *Mutat. Res*. 285:125-144; Hayashi (1992) *Genet. Anal Tech. Appl*. 9:73-79). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet*. 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem*. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res*. 17:2437-2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoris or family history of a disease or illness involving a gene encoding a polypeptide of the invention. Furthermore, any cell type or tissue, preferably peripheral blood leukocytes, in which the polypeptide of the invention is expressed may be utilized in the prognostic assays described herein.

3. Pharmacogenomics

Agents, or modulators which have a stimulatory or inhibitory effect on activity or expression of a polypeptide of the invention as identified by a screening assay described herein can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a polypeptide of the invention, expression of a nucleic acid of the invention, or mutation content of a gene of the invention in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254-266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a polypeptide of the invention, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenctic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

4. Monitoring of Effects During Clinical Trials

Monitoring the influence of agents (e.g., drugs, compounds) on the expression or activity of a polypeptide of the invention (e.g., the ability to modulate aberrant cell proliferation chemotaxis, and/or differentiation) can be applied not only in basic drug screening, but also in clinical trials. For example, the effectiveness of an agent, as determined by a screening assay as described herein, to increase gene expression, protein levels or protein activity, can be monitored in clinical trials of subjects exhibiting decreased gene expression, protein levels, or protein activity. Alternatively, the effectiveness of an agent, as determined by a screening assay, to decrease gene expression, protein levels or protein activity, can be monitored in clinical trials of subjects exhibiting increased gene expression, protein levels, or protein activity. In such clinical trials, expression or activity of a polypeptide of the invention and preferably, that of other polypeptide that have been implicated in for example, a cellular proliferation disorder, can be used as a marker of the immune responsiveness of a particular cell.

For example, and not by way of limitation, genes, including those of the invention, that are modulated in cells by treatment with an agent (e.g., compound, drug or small molecule) which modulates activity or expression of a polypeptide of the invention (e.g., as identified in a screening assay described herein) can be identified. Thus, to study the effect of agents on cellular proliferation disorders, for example, in a clinical trial, cells can be isolated and RNA prepared and analyzed for the levels of expression of a gene of the invention and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of a gene of the invention or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of the polypeptide or nucleic acid of the invention in the preadministration sample; (iii) obtaining one or more post-administration samples from the subject; (iv) detecting the level the of the polypeptide or nucleic acid of the invention in the post-administration samples; (v) comparing the level of the polypeptide or nucleic acid of the invention in the pre-administration sample with the level of the polypeptide or nucleic acid of the invention in the post-administration sample or samples; and (vi) altering the administration of the agent to the subject accordingly. For example, increased administration of the agent may be desirable to increase the expression or activity of the polypeptide to higher levels than detected, i.e., to increase the effectiveness of the agent. Alternatively, decreased administration of the agent may be desirable to decrease expression or activity of the polypeptide to lower levels than detected, i.e., to decrease the effectiveness of the agent.

C. Methods of Treatment

The present invention provides for both prophylactic and therapeutic methods of treating a subject at risk of (or susceptible to) a disorder or having a disorder associated with aberrant expression or activity of a polypeptide of the invention. For example, disorders characterized by abberant expression or activity of the polypeptides of the invention include proliferative disorders such as psoriasis and cancer. In addition, the polypeptides of the invention can be used to promote hair growth, promote wound healing, as well as other uses described herein.

1. Prophylactic Methods

In one aspect, the invention provides a method for preventing in a subject, a disease or condition associated with an aberrant expression or activity of a polypeptide of the invention, by administering to the subject an agent which modulates expression or at least one activity of the polypeptide. Subjects at risk for a disease which is caused or contributed to by aberrant expression or activity of a polypeptide of the invention can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. For example, an antagonist of an ELVIS protein may be used to treat a proliferative disorder, e.g., psoriasis, associated with abberant ELVIS expression or activity. The appropriate agent can be determined based on screening assays described herein.

2. Therapeutic Methods

Another aspect of the invention pertains to methods of modulating expression or activity of a polypeptide of the invention for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptidomimetic, or other small molecule. In one embodiment, the agent stimulates one or more of the biological activities of the polypeptide. Examples of such stimulatory agents include the active polypeptide of the invention and a nucleic acid molecule encoding the polypeptide of the invention that has been introduced into the cell. In another embodiment, the agent inhibits one or more of the biological activities of the polypeptide of the invention. Examples of such inhibitory agents include antisense nucleic acid molecules and antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a polypeptide of the invention. In one embodiment, the method involves administering an agent (e.g., an agent identified by a screening assay described herein), or combination of agents that modulates (e.g., upregulates or downregulates) expression or activity. In another embodiment, the method involves administering a polypeptide of the invention or a nucleic acid molecule of the invention as therapy to compensate for reduced or aberrant expression or activity of the polypeptide.

Stimulation of activity is desirable in situations in which activity or expression is abnormally low or downregulated and/or in which increased activity is likely to have a beneficial effect, e.g., in wound healing. Conversely, inhibition of activity is desirable in situations in which activity or expression is abnormally high or upregulated and/or in which decreased activity is likely to have a beneficial effect, e.g., in treatment of a proliferative disorder such as psoriasis.

Modulators of the expression or activity of a protein of the invention may also be sued in treatment of contact dermatitis, in treatment of burns, in modulation of epithelial cell growth and in treatment of hair loss or unwanted hair growth.

This invention is further illustrated by the following examples which should not be construed as limiting. The contents of all references, patents and published patent applications cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule comprising a contiguous open reading frame which encodes a polypeptide comprising an amino acid sequence at least 95% identical to the amino acid sequence of SEQ ID NO: 5, 16, or 19, or an amino acid sequence encoded by the cDNA insert of the plasmid deposited with ATCC as Accession Number 98982, or the complement thereof, wherein the polypeptide stimulates growth and differentiation of keratinocytes.

2. The isolated nucleic acid molecule of claim 1, wherein the nucleic acid molecule comprises a nucleotide sequence which encodes a polypeptide comprising the amino acid sequence of SEQ ID NO: 5, 16, or 19, or an amino acid sequence encoded by the cDNA insert of the plasmid deposited with ATCC as Accession Number 98982.

3. The isolated nucleic acid molecule of claim 2, wherein the nucleic acid molecule comprises a nucleotide sequence which encodes a polypeptide comprising the amino acid sequence of SEQ ID NO:5.

4. The isolated nucleic acid molecule of claim 1, comprising the nucleotide sequence of SEQ ID NO:4 or 6, or the nucleotide sequence of the cDNA insert of the plasmid deposited with ATCC as Accession Number 98982.

5. The isolated nucleic acid molecule of claim 1, wherein the nucleic acid molecule comprises the nucleotide sequence of SEQ ID NO: 4 or 6.

6. The nucleic acid molecule of claim 1, which encodes a polypeptide comprising an EGF domain.

7. The nucleic acid molecule of claim 6, wherein the EGF domain comprises the amino acid sequence of SEQ ID NO:16.

8. The nucleic acid molecule of claim 2 comprising a nucleotide sequence which encodes a polypeptide comprising the amino acid sequence of SEQ ID NO:19.

9. The isolated nucleic acid molecule of claim 8, wherein the nucleic acid molecule comprises nucleotides 61-309 of SEQ ID NO:6.

10. The nucleic acid molecule of claim 1 or 6, further comprising a heterologous nucleic acid sequence.

11. A vector comprising the nucleic acid molecule of claim 1 or 6.

12. The vector of claim 11, further comprising a nucleic acid sequence which regulates expression of a polypeptide encoded by the nucleic acid molecule.

13. A vector comprising the nucleic acid molecule of claim 10.

14. The vector of claim 13, further comprising a nucleic acid sequence which regulates expression of a polypeptide encoded by the nucleic acid molecule.

15. An isolated host cell comprising the vector of claim 11.

16. An isolated host cell comprising the vector of claim 12.

17. An isolated host cell comprising the vector of claim 13.

18. An isolated host cell comprising the vector of claim 14.

19. An isolated host cell comprising the nucleic acid molecule of claim 1 or 8.

20. An isolated host cell genetically engineered to express the nucleic acid molecule of claim 1 or 6.

21. The isolated host cell of claim 15 which is a mammalian host cell.

22. The isolated host cell of claim 16 which is a mammalian host cell.

23. The isolated host cell of claim 17 which is a mammalian host cell.

24. The isolated host cell of claim 18 which is a mammalian host cell.

25. The isolated host cell of claim 19 which is a mammalian host cell.

26. The isolated host cell of claim 20 which is a mammalian host cell.

27. A method for expressing a polypeptide comprising culturing the isolated host cell of claim 21 under conditions in which the nucleic acid molecule is expressed.

28. A method for expressing a polypeptide comprising culturing the isolated host cell of claim 22 under conditions in which the nucleic acid molecule is expressed.

29. A method for expressing a polypeptide comprising culturing the isolated host cell of claim 23 under conditions in which the nucleic acid molecule is expressed.

30. A method for expressing a polypeptide comprising culturing the isolated host cell of claim 24 under conditions in which the nucleic acid molecule is expressed.

31. A method for expressing a polypeptide comprising culturing the isolated host cell of claim 25 under conditions in which the nucleic acid molecule is expressed.

32. A method for expressing a polypeptide comprising culturing the isolated host cell of claim 26 under conditions in which the nucleic acid molecule is expressed.

33. A method for detecting the presence of a nucleic acid molecule of claim 1 in a sample, comprising the steps of:
a) contacting the sample with a nucleic acid probe or primer which selectively hybridizes to the nucleic acid molecule; and
b) determining whether the nucleic acid probe or primer binds to a nucleic acid molecule in the sample.

34. The method of claim 33, wherein the sample comprises mRNA molecules and is contacted with a nucleic acid probe.

35. The isolated nucleic acid molecule of claim 1, wherein the polypeptide induces blister formation of keratinocytes in a cell culture.

* * * * *

UNITED STATES PATENT AND TRADEMARK OFFICE
CERTIFICATE OF CORRECTION

PATENT NO. : 7,294,482 B2  
APPLICATION NO. : 10/345764  
DATED : November 13, 2007  
INVENTOR(S) : Samantha J. Busfield and David P. Gearing Page 1 of 1

It is certified that error appears in the above-identified patent and that said Letters Patent is hereby corrected as shown below:

Column 71, claim 10, line 52, delete "claim 1 or 6" and insert --claim 1 or 8--

Column 71, claim 11, line 55, delete "claim 1 or 6" and insert --claim 1 or 8--

Column 72, claim 20, line 21, delete "claim 1 or 6" and insert --claim 1 or 8--

Signed and Sealed this

Seventeenth Day of June, 2008

JON W. DUDAS  
*Director of the United States Patent and Trademark Office*